US007276617B2

(12) United States Patent
Sotoyama et al.

(10) Patent No.: US 7,276,617 B2
(45) Date of Patent: Oct. 2, 2007

(54) ORGANOMETALLIC COMPLEX, LUMINESCENT SOLID, ORGANIC EL ELEMENT AND ORGANIC EL DISPLAY

(75) Inventors: Wataru Sotoyama, Minami-Ashigara (JP); Tasuku Satoh, Minami-Ashigara (JP); Hiroyuki Sato, Kawasaki (JP); Azuma Matsuura, Kawasaki (JP); Norio Sawatari, Kawasaki (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/376,274

(22) Filed: Mar. 16, 2006

(65) Prior Publication Data
US 2006/0243966 A1    Nov. 2, 2006

(30) Foreign Application Priority Data
Mar. 17, 2005    (JP)    ............... 2005-076963

(51) Int. Cl.
*C07F 15/00*    (2006.01)
*C07F 9/66*    (2006.01)
*H01L 51/00*    (2006.01)

(52) U.S. Cl. ............. 556/35; 548/402; 313/504; 257/40

(58) Field of Classification Search ........... 556/35; 257/40; 548/402; 313/504
See application file for complete search history.

(56) References Cited

U.S. PATENT DOCUMENTS

2006/0093854 A1*    5/2006    Sotoyama et al. ......... 428/690

FOREIGN PATENT DOCUMENTS

JP    2002-363552 A    12/2002

OTHER PUBLICATIONS

Sotoyama et al., Applied Physics Letters, vol. 86, 153505/1-153505/3 (published online Apr. 6, 2005).*
Hoogervorst et al., Organometallics, vol. 233, No. 5, pp. 1161-1164 (Feb. 3, 2004).*
Takenaka et al., Journal of American Chemical Society, vol. 127, No. 35, pp. 12273-12281 (Aug. 13, 2005).*
C.W. Tang et al., Appl. Phys. Lett. 51 (12), Sep. 21, 1987, pp. 913 to 915.
C. W. Tang et al., J. Appl. Phys. 65 (9) May 1, 1989, pp. 3610 to 3616.
M. A. Baldo et al., Nature vol. 395, Sep. 10, 1998, pp. 151 to 154.
M.A. Baldo et al., Applied Physics Letters vol. 75, No. 1, Jul. 5, 1999, pp. 4 to 6.
J.A. Williams et al., Inorganic Chemistry, vol. 42, No. 26, 2003 pp. 8609 to 8611.

* cited by examiner

*Primary Examiner*—Porfirio Nazario-Gonzalez
(74) *Attorney, Agent, or Firm*—Birch, Stewart, Kolasch & Birch, LLP

(57) ABSTRACT

An object of the invention is to provide an organic EL element which uses an organometallic complex emitting light by phosphorescence and which represents excellent luminous efficiency, etc; or the like. The organic EL element of the invention includes the organometallic complex, where the organometallic complex includes a metal atom, and a tridentate ligand, where the tridentate ligand binds to the metal atom tridentately via two nitrogen atoms and a carbon atom, and the carbon atom is located between the two nitrogen atoms, and where the tridentate ligand has two azomethine bonds (—C=N—), and each nitrogen atom in the azomethine bonds coordinates to the metal atom. Preferably, in one aspect, the organometallic complex includes a monodentate ligand which binds to the metal atom monodentately, and in another aspect, the metal atom is Pt.

13 Claims, 5 Drawing Sheets

US 7,276,617 B2

ORGANOMETALLIC COMPLEX, LUMINESCENT SOLID, ORGANIC EL ELEMENT AND ORGANIC EL DISPLAY

BACKGROUND OF THE INVENTION

1. Field of the Invention

The present invention relates to organometallic complexes and luminescent solids that emit light by phosphorescence and that are suitable for the light-emitting material, color conversion material, etc. of organic EL elements, lighting apparatuses, etc. The present invention also relates to organic EL elements employing the organometallic complexes or luminescent solids, and to organic EL displays employing the organic EL elements.

2. Description of the Related Art

An organic EL element has a structure in which one or a plurality of thin organic material layers is interposed between a negative electrode and a positive electrode. In the organic EL, a hole and an electron are injected into the organic material layer from the positive electrode and the negative electrode, respectively, the recombination energy, which is generated when the hole and electron are recombined in the organic material layer, causes the emission center of the light-emitting material in the organic material layer excited, and when the light-emitting material falls from an excited state to a ground state, light is emitted. The organic EL element is a light-emitting element which uses this emitted light. The organic EL element has features such as self-luminousness and rapid response, exhibits satisfactory visual properties, is super-slim and lightweight, and is excellent in rapid response and movie display. Thus, it is predicted to be widely utilized for flat panel displays such as a full-color display. Particularly, since a two-layered (multilayered) organic EL element comprising an organic thin film having hole transport property (hole-transporting layer) and an organic thin film having electron transport property (electron-transporting layer) was reported (see, C. W. Tang and S. A. VanSlyke, Applied Physics Letters vol. 51, 913 (1987)), the organic EL elements have been attracting attention as large area light-emitting elements which can emit light at as low voltage as 10 V or less.

In the organic EL element, in order to improve luminous efficiency, a light-emitting layer is proposed that is produced from a fluorescence luminescent host material, as the main material, doped with a small amount of dye having a higher fluorescence luminescence as a guest material and that exhibits high emission efficiency (see, "C. W. Tang, S. A. VanSlyke, and C. H. Chen, Journal of Applied Physics vol. 65, 3610, 1989").

Moreover, recently, it was shown that it is possible to improve the luminous efficiency of the organic EL element by employing, as a light-emitting material, a phosphorescence luminescent material, which uses emission from the excitation triplet state of molecule, instead of the fluorescence luminescent material, which attracts attention (see, M. A. Baldo, et al., Nature vol. 395, 151 (1998), and M. A. Baldo, et al., Applied Physics Letters vol. 75, 4 (1999)). Light emission from organic material is classified into fluorescence and phosphorescence by the properties of excited state causing emission. In organic EL elements, fluorescence luminescent materials have been utilized due to the reason that general organic material does not give phosphorescence at room temperature. From EL emission mechanism, it is anticipated that the phosphorescent state is generated four times as much as the fluorescent state. Thus, in recent years, attention has been made on the application of a heavy metal complex, which shows phosphorescence at room temperature, to a light-emitting material as a means for achieving high efficiency in EL elements. In case of phosphorescence luminescent material, however, there are few materials which emit strong phosphorescence at room temperature, causing a problem that the material can only be selected from a narrow range of materials.

One of known examples of organic EL elements using an organometallic complex emitting phosphorescence at room temperature is a metal complex comprising a N^N^C type tridentate ligand consisting of two coordinate bonds between a platinum element and nitrogen atom, and one direct bond between the platinum element and a carbon atom, wherein two nitrogen atoms involved in the coordinate bond are arranged adjacent to each other (see, Japanese Patent Application Laid-Open No. 2002-363552).

However, the phosphorescent efficiency at room temperature of this metal complex is not sufficient, and thus there is a problem that the organic EL element using this metal complex has a low light emitting efficiency. On the other hand, it has been reported that platinum complexes comprising a N^C^N type tridentate ligand and a Cl atom which binds to the platinum element emit phosphorescence in solution with higher efficiency than the N^N^C type platinum complexes, wherein the N^C^N type tridentate ligand consists of two coordinate bonds between a platinum element and nitrogen atom, and one direct bond between the platinum element and a carbon atom, and the carbon atom is arranged between two nitrogen atoms involved in the coordinate bond (see, J. A. G. Williams et al., Inorganic Chemistry Vol. 42, 8609 (2003)). In case of the organic EL element using this metal complex, however, there was a problem that when a N^C^N type tridentate ligand is synthesized, organic compounds such as an organotin compound, which is difficult to synthesize and handle, must be used as a raw material.

An object of the present invention is to solve conventional problems mentioned above and to achieve the following objects. Specifically, an object of the present invention is to provide an organometallic complex and luminescent solid that emit high-intensity light by phosphorescence and that are suitable for a light-emitting material, color conversion material, etc. of organic EL elements, lighting apparatuses, etc. Another object of the present invention is to provide an organic EL element which uses the organometallic complex or luminescent solid and represents excellent luminous efficiency, etc. A further object of the present invention is to provide an organic EL display which uses the organic EL element, represents high quality, allows a constant average driving current independently of light-emitting pixels, and has satisfactory color balance without changing the light-emitting area; and which is suitable for, e.g. full-color displays.

SUMMARY OF THE INVENTION

The present inventors have investigated vigorously in order to solve the problems described above, and have found the following experiences or discoveries. Specifically, a N^C^N type tridentate ligand that includes two nitrogen atoms, which coordinate to the metal atom, and a carbon atom, the carbon atom being arranged between the two nitrogen atoms, and that has two azomethine bonds (—C=N—), can be easily synthesized from a raw material which is easily available. The organometallic complex containing the tridentate ligand and the metal atom emits high-intensity light by phosphorescence, exhibits satisfactory sublimation property suitable for organic EL elements, can form a satisfactory neat film, dope film, etc. by means of vapor deposition, and is suitable for the light-emitting material of e.g. organic EL elements or lighting apparatuses. Luminescent solids including the organometallic complex, and organic EL elements and organic EL displays employing the organometallic complex may represent excellent luminous efficiency, etc.

The invention is based on the above-mentioned experiences or discoveries by the present inventors.

The organometallic complex of the invention includes (1) a metal atom; and (2) a tridentate ligand which binds to the metal atom tridentately via two nitrogen atoms and a carbon atom, and the carbon atom being located between the two nitrogen atoms, wherein the tridentate ligand has two azomethine bonds (—C=N—), and each nitrogen atom in the azomethine bonds coordinates to the metal atom.

Light emission from organic material is classified into fluorescence and phosphorescence by the properties of excited state causing emission. Conventionally, fluorescent materials have been used as a light-emitting material, color conversion material, etc. in organic EL elements, lighting apparatuses, etc. due to the reason that organic material does not generally give phosphorescence. From EL emission mechanism, however, it is anticipated that the phosphorescent state is generated 4 times as much as the fluorescent state. Thus, it is effective to apply a metal complex giving phosphorescence at room temperature to a light-emitting material in order to achieve high efficiency EL elements and such complex has attracted attention in recent years. The organometallic complex of the invention gives strong phosphorescence with high luminance. Thus, high luminous efficiency, theoretically maximum 100%, can be achieved, while the internal quantum efficiency of the EL elements employing a fluorescent material is 25% at most. Therefore, the organometallic complex emitting high-intensity light by phosphorescence is suitable for the light-emitting material, etc. of e.g. organic EL elements. Emission color can be changed by changing the skeleton structure, the types or number of the substituent group, or the like of the specific tridentate ligand (N^C^N type) in the organometallic complex of the invention.

The luminescent solid of the invention includes the organometallic complex of the invention. The luminescent solid including the organometallic complex of the invention may represent excellent luminous efficiency, etc. and can be suitably used in lighting apparatuses, display devices, etc.

The organic EL element of the invention includes a positive electrode, a negative electrode, and an organic thin layer between the positive electrode and the negative electrode, wherein the organic thin layer includes the organometallic complex. The organic EL element of the invention including the organometallic complex of the invention may represent excellent luminous efficiency, etc. and can be suitably used in lighting apparatuses, display devices, etc.

The organic EL display of the invention is formed from the organic EL element of the invention. The organic EL display of the invention employing the organic EL element of the invention may represent excellent luminous efficiency, etc.

Figure 1:
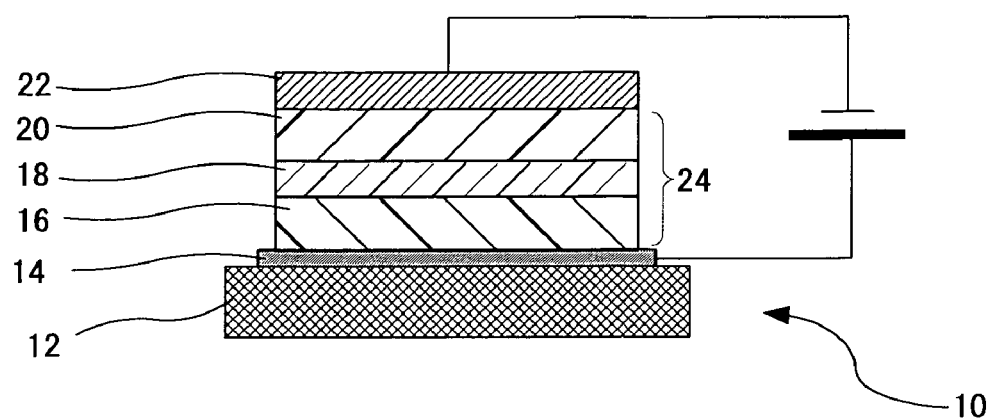
FIG. 1 is a schematic view showing an exemplary layer configuration of an organic EL element according to the invention.

DESCRIPTION OF THE PREFERRED EMBODIMENTS (Organometallic Complex and Luminescent Solid)

The organometallic complex of the invention comprises a metal atom and a specific tridentate ligand which binds to the metal atom tridentately, preferably comprises a monodentate ligand which binds to the metal atom monodentately, and further comprises other ligands properly selected according to necessity.

The luminescent solid of the invention comprises the organometallic complex of the invention, and further comprises other components properly selected according to necessity. The luminescent solid may be any form without limitation and may be properly selected depending on the application. Examples thereof include crystals, thin films, and the like. The content of the organocomplex metal in the luminescent solid is not particularly limited and may be properly selected depending on the application, normally 0.1% by mass to 50% by mass and preferably 0.5% by mass to 20% by mass, by which emission with high efficiency and prolonged life time can be obtained.

-Metal Atom-

The metal atom acts as a central metal in the organometallic complex. The metal atom is not particularly limited and may be properly selected depending on the application. Examples thereof include Fe, Co, Ni, Ru, Rh, Pd, Os, IR, Pt, and the like. One of these are contained per molecule of the organometallic complex. As each metal atom in the organometallic complex consisting of two or more molecules, one kind of the metal atom may be used, or two or more kinds may be used. Among the metal atoms, Pt is particularly preferable (in this case, the organometallic complex is platinum complex).

-Tridentate Ligand-

The tridentate ligand is not particularly limited as long as it binds to the metal atom tridentately via two nitrogen atoms and a carbon atom, the carbon atom is located between the two nitrogen atoms (N^C^N type), the tridentate ligand has two azomethine bonds (—C=N—), and each nitrogen atom in the azomethine bonds coordinates to the metal atom, and the tridentate ligand may be properly selected depending on the application. For example, such a tridentate ligand that has the structure expressed by the following formula (2) is preferable.

The carbon atom constituting the azomethine bond (—C=N—) has a hydrogen atom and is saturated. Namely, the carbon atom and nitrogen atom constituting the azomethine bond (—C=N—) do not form a ring structure.

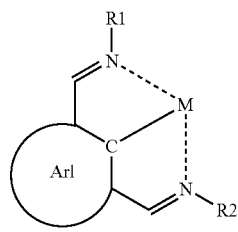

general formula (2)

In the formula (2), M represents a metal atom. Ar1 represents a ring structure which may have a substituent group. C in the Ar1 represents a carbon atom constituting the ring structure represented by the Ar1. R1 and R2 may be identical or different each other, and each represents an alkyl group or aryl group, which may have a substituent group. In the formula (2), M represents the above-mentioned metal atom to which the Ar1 binds and is not part of the structure of the Ar1.

The Ar1 is not particularly limited as long as it has the ring structure and may be properly selected depending on the application. The Ar1 is, for example, one selected from a five-membered ring group, six-membered ring group, and condensed ring of these, and is preferably one having a substituted or unsubstituted benzene ring in terms of easy synthesis. Suitable examples include those represented by the structure shown in the following structural formulae (1) to (5), and the like.

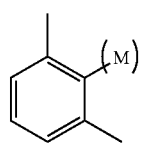

structural formula (1)

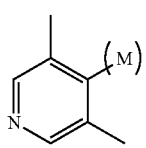

structural formula (2)

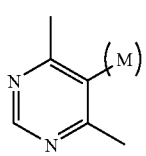

structural formula (3)

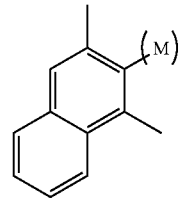

structural formula (4)

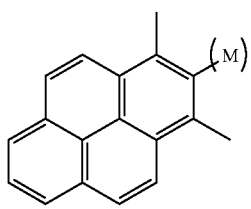

structural formula (5)

In the structural formulae (1) to (5), M represents the metal atom. In these structural formulae, M represents the above-mentioned metal atom to which the Ar1 binds and is not part of the structure of the Ar1.

The R1 and R2 are preferably identical in that the tridentate ligand is synthesized extremely easily.

The R1 and R2 are not particularly limited and may be properly selected depending on the application, but the R1 and R2 are preferably, for example, an alkyl group, cycloalkyl group, aryl group, or the like, and more preferably those having a substituted or unsubstituted benzene ring in terms of easy synthesis. Preferable specific examples of the R1 and R2 include those expressed by the following structural formulae (6) to (16), and the like.

structural formula (6)

structural formula (7)

structural formula (8)

structural formula (9)

structural formula (10)

structural formula (11)

structural formula (12)
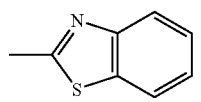

structural formula (13)
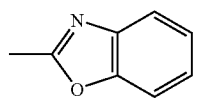

structural formula (14)
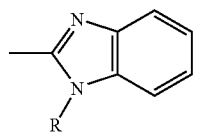

structural formula (15)

structural formula (16)
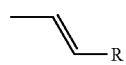

In the structural formulae (6) to (16), R represents a hydrogen atom or substituent group.

The hydrogen atom in the Ar1, R1, and R2 may be substituted. Suitable examples of the substituent group include a halogen atom, cyano groups, alkoxy groups, amino groups, alkyl groups, alkyl acetate groups, cycloalkyl groups, aryl groups, aryloxy groups, and the like. These substituent groups may be further substituted.

Preferable specific examples of the tridentate ligand include those expressed by the following structural formulae (17) to (26), and the like.

structural formula (17)
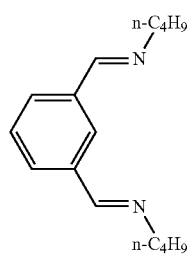

structural formula (18)
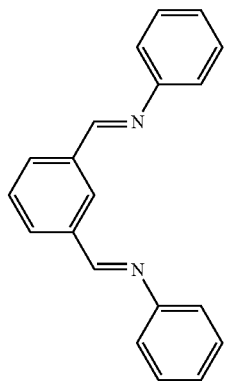

structural formula (19)
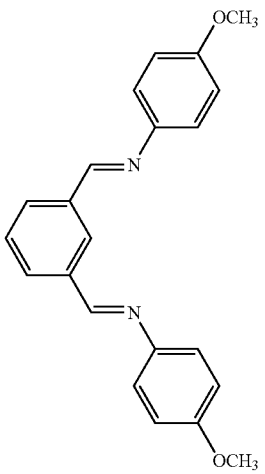

structural formula (20)
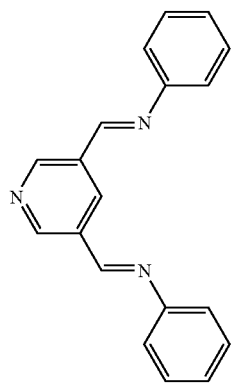

structural formula (21)
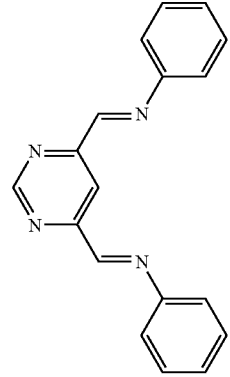

structural formula (22)
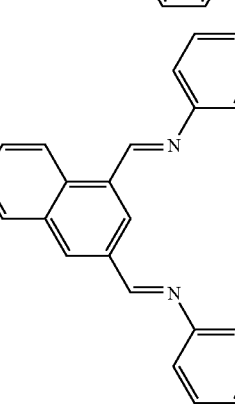

-continued

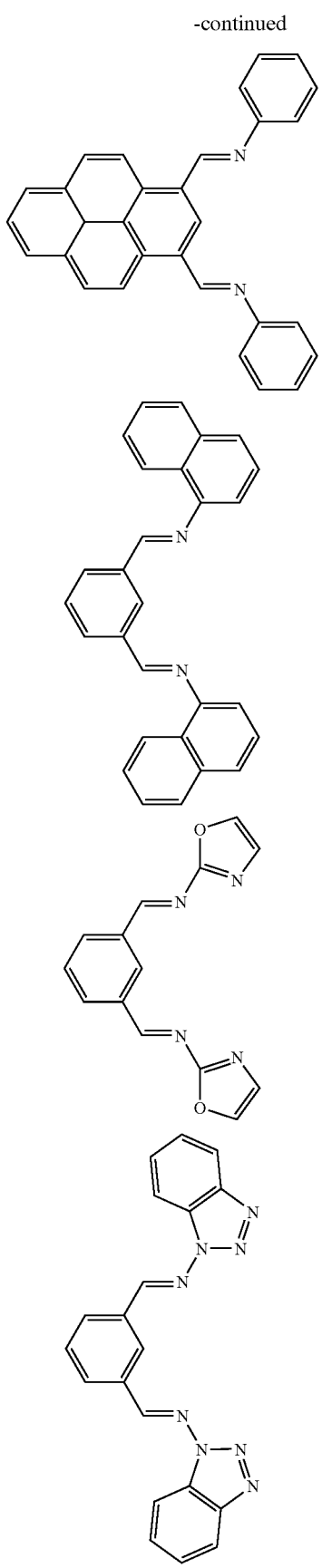

structural formula (23)

structural formula (24)

structural formula (25)

structural formula (26)

-Monodentate Ligand-

The monodentate ligand is a ligand which binds to the metal atom monodentately. Suitable examples of the monodentate ligand include a halogen atom; a group which binds to the metal atom via one atom selected from a C atom, N atom, O atom, and S atom; and the like.

The group which binds to the metal atom via one atom selected from a C atom, N atom, O atom, and S atom is not particularly limited and may be properly selected depending on the application, including, for example, those expressed by the following structural formulae (27) to (48), and the like. Among these, one expressed by the following structural formula (30) is preferable in terms of easy synthesis and high light emitting efficiency of its products.

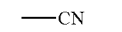 structural formula (27)

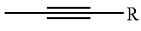 structural formula (28)

 structural formula (29)

structural formula (30)

—O—R structural formula (31)

—S—R structural formula (32)

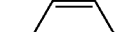

structural formula (33)

structural formula (34)

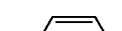

structural formula (35)

structural formula (36)

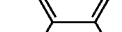

structural formula (37)

structural formula (38)

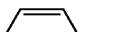

structural formula (39)

structural formula (40)

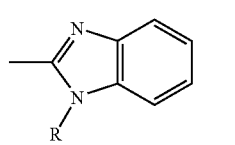

structural formula (41)

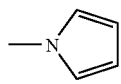

structural formula (42)

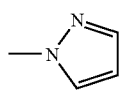

structural formula (43)

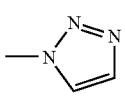

structural formula (44)

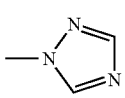

structural formula (45)

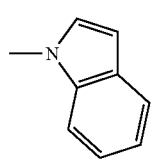

structural formula (46)

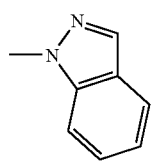

structural formula (47)

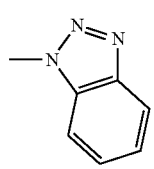

structural formula (48)

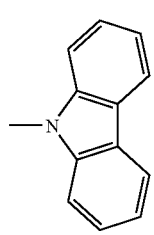

In the structural formulae (27) to (48), hydrogen atom may be substituted with organic groups or halogen atoms, and R represents one of a hydrogen atom, alkyl groups, and aryl groups.

Examples of the halogen atom include a fluorine atom, chlorine atom, bromine atom, and the like. Among these, fluorine atom is preferable in terms of low reactivity and excellent decay resistance.

Examples of the alkyl group include a methyl group, ethyl group, propyl group, butyl group, isopropyl group, and the like. Among these, methyl group is preferable.

Examples of the aryl group include a phenyl group, toluyl group, and the like. Among these, phenyl group is preferable.

Among the monodentate ligands, those allowing the entire charge of the organometallic complex to be neutral are preferable in that the organometallic complex can be provided with sublimation property.

The other ligands are not particularly limited and may be properly selected depending on the application, but preferably those making the entire charge of the organometallic complex neutral and preferably those which can be synthesized easily in that the organometallic complex can be provided with sublimation property.

-Exemplary Structure of Organometallic Complex-

As the exemplary structure of the organometallic complex of the invention, for example, the organometallic complex expressed by the following general formula (1) is suitable. The organometallic complex in which the above-mentioned tridentate ligand and the above-mentioned monodentate ligand bind to the metal atom is preferable.

general formula (1)

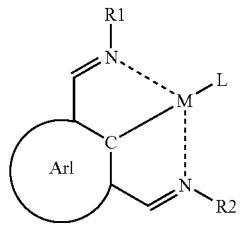

In the general formula (1), M represents a metal atom. Ar1 represents a ring structure which may have a substituent group, and binds to the M. The nitrogen atoms (N) of two azomethine bonds (—C═N—) each bind to the M. Ar1 and nitrogen atoms form a tridentate ligand as a whole which binds to the M tridentately. C in the Ar1 represents a carbon atom constituting the ring structure represented by the Ar1. R1 and R2 may be identical or different each other, and each represents an alkyl group or aryl group, which may have a substituent group. L represents a monodentate ligand.

In the general formula (1), the M includes the above-described metal atoms and is preferably Pt (When the metal atom is Pt, the organometallic complex is a platinum complex).

The Ar1 is not particularly limited as long as it has the ring structure and may be properly selected depending on the application, but the Ar1 is preferably one selected from a five-membered ring group, six-membered ring group, and condensed ring of these.

The organometallic complex represented by the general formula (1) is electrically neutral and exhibits sublimation property in vacuo. Therefore, the organometallic complex represented by the general formula (1) is advantageous in that when forming a thin film, not only known coating methods, but also a vacuum deposition method can be suitably applied.

Preferable specific examples of the organometallic complex include those represented by the structure shown in the following structural formulae (49) to (62).
structural formula (49)
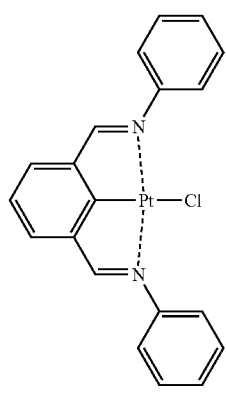
structural formula (50)
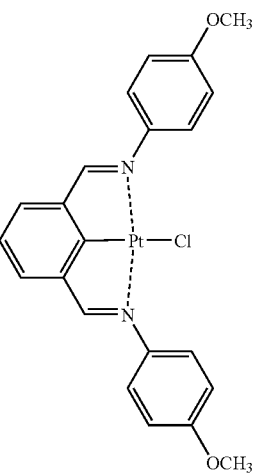
structural formula (51)
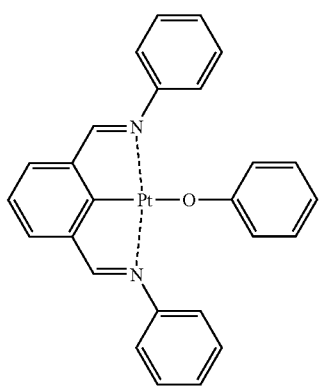
structural formula (52)
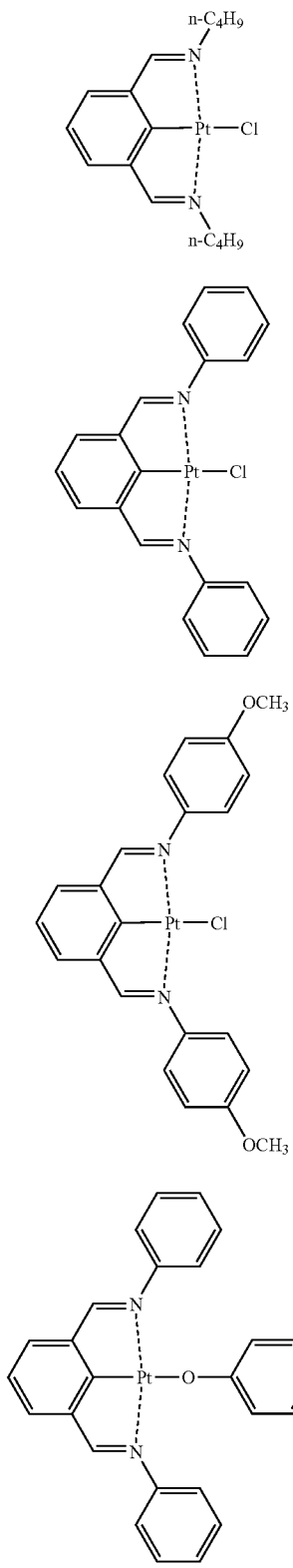
structural formula (53)
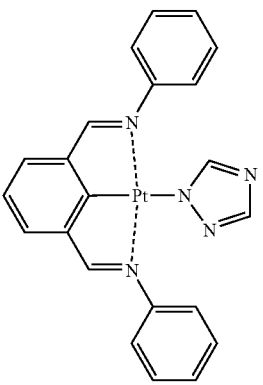
structural formula (54)
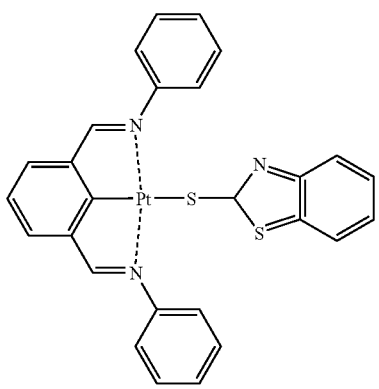
structural formula (55)
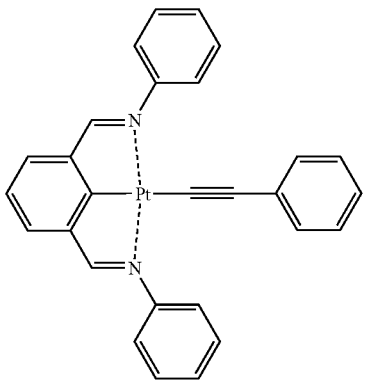
structural formula (56)
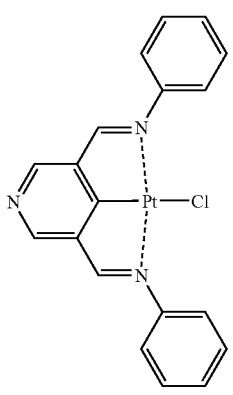

structural formula (57)

structural formula (58)

structural formula (59)

structural formula (60)

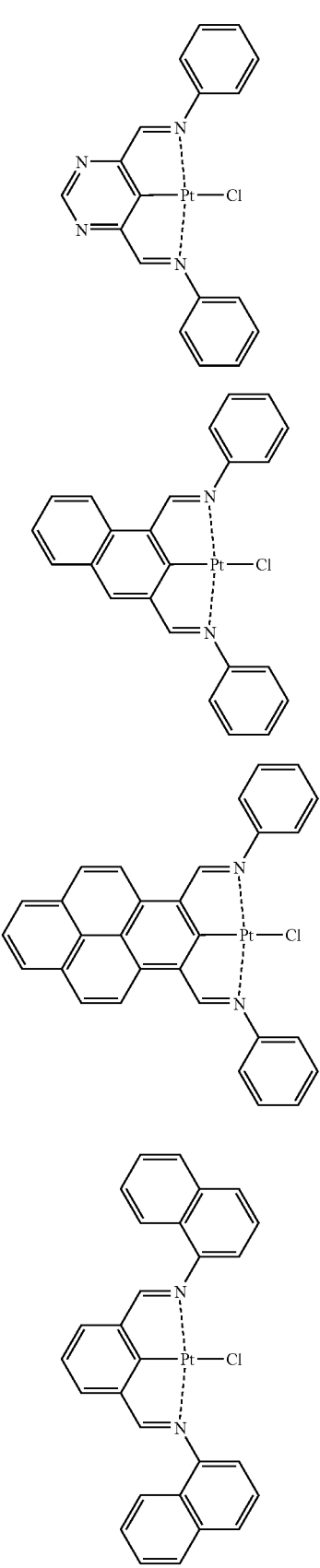

structural formula (61)

structural formula (62)

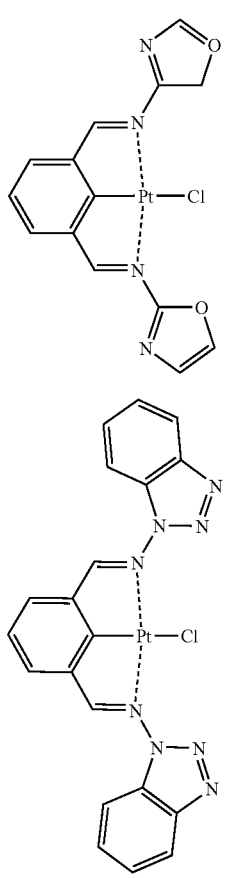

Photoluminescence (P.L.: hereinafter, may be simply abbreviated as "PL") quantum yield of the organometallic complex of the invention, determined using a thin film of aluminum quinoline complex (Alq$_3$) (PL quantum yield=22%) as reference, is preferably 70% or more and more preferably 90% or more, where the thin film of aluminum quinoline complex is prepared so as to have the same thickness as that of the organometallic complex of the invention when prepared as a thin film.

Figure 9:
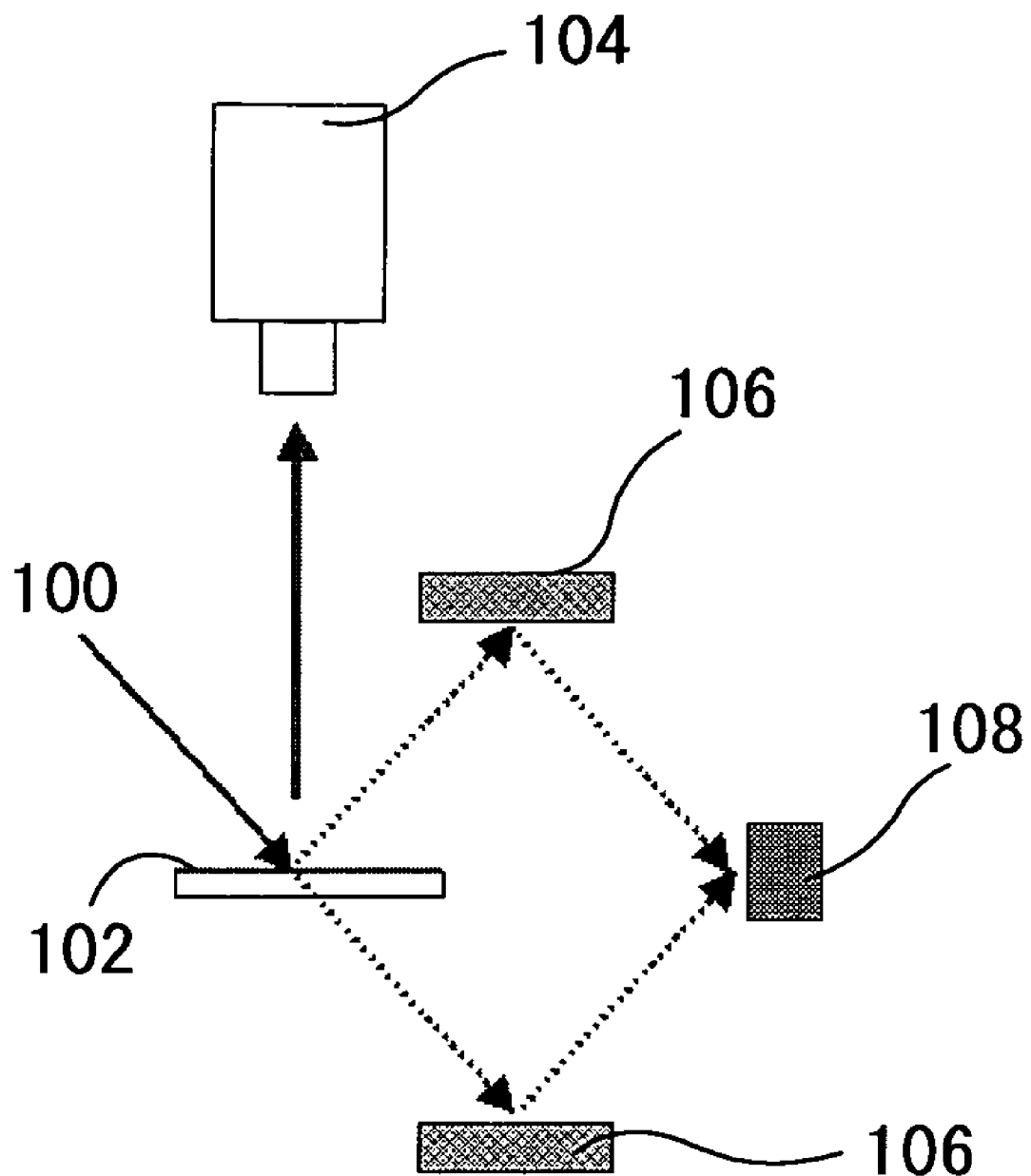
FIG. 9 is a schematic view for explaining an overview of an experiment for calculating a phosphorescence quantum yield.

The PL quantum yield, for example, can be measured and calculated as follows. Specifically, as shown in FIG. 9, thin film of sample 102 on a transparent substrate is obliquely irradiated with excitation light (365-nm continuous light) 100 from light source. The PL spectrum of the thin film is measured using spectroradiometer (CS-1000, manufactured by Minolta Co., Ltd.) 104 and the PL photon number [P(sample)] is calculated by conversion. Simultaneously with the luminescence measurement, the excitation light transmitted through and reflected from the sample are absorbed with mirror 106, and the total intensity [I(sample)] is detected using photodiode 108. Subsequently, similar measurement is carried out with respect to the thin film of Alq3 as reference (PL quantum yield 22%) to thereby determine the PL photon number [P(ref.)] and total intensity of transmitted and reflected excitation light [I(ref)] of reference. Next, the total intensity of transmitted and reflected excitation light of the transparent substrate alone [I(substrate)] is measured. The PL quantum yield of the thin film of the sample can be calculated using the following mathematical formula.

$$(PL \text{ quantum efficiency}) = \frac{P(\text{sample})/[I(\text{substrate}) - I(\text{sample})]}{P(ref.)/[I(\text{substrate}) - I(ref.)]} \times 22\%$$

-Synthetic Method-

The synthetic method of the organometallic complex of the invention is not particularly limited and may be properly selected depending on the application. Suitable examples of the synthetic method include a method in which the tridentate ligand (N^C^N type) and metal halide having the metal atom and a halogen atom (chlorine atom) are allowed to react according to an appropriately selected condition to thereby obtain the organometallic complex of the invention containing the tridentate ligand and a halogen; further a method in which the organometallic complex of the invention containing the tridentate ligand and a halogen, and hydrogen substitution or alkali metal substitution of the monodentate ligand are allowed to react according to an appropriately selected condition to thereby obtain the organometallic complex of the invention containing the tridentate ligand and the monodentate ligand; and the like.

The above-mentioned reaction can be suitably performed in the presence of catalyst, and the catalyst is not particularly limited and may be properly selected depending on the application. Suitable examples include copper salt-organic amine catalysts and the like. These may be used alone or two or more may be used in combination.

-Application or the Like-

The organometallic complex and luminescent solid comprising the organometallic complex of the invention is excellent in PL quantum yield as described above and exhibits high emission efficiency, and thus can be suitably used in a variety of fields. Particularly, the organometallic complex and luminescent solid can be suitably used in one of organic EL elements and lighting apparatuses since a desired emission color with high luminance and prolonged life time can be obtained. In the organic EL display in which the organic EL element is used, a combination of organic EL elements for each color of red, green, and blue is used as one pixel. In this case, three colors of organic EL elements are required. The emission color of the organometallic complex of the invention can be adjusted or changed by appropriately changing the molecular structure of the tridentate ligand, by which emission of each color of red, green, and blue can be obtained. Therefore, the application of the organometallic complex to the organic EL element is advantageous.

(Organic EL Element)

The organic EL element of the invention comprises a positive electrode, a negative electrode, and an organic thin layer between the positive electrode and the negative electrode, wherein the organic thin layer comprises the organometallic complex of the invention, and the organic EL element of the invention further comprises appropriately selected other layers or members.

The organic thin layer is not particularly limited and may be properly selected depending on the application. For example, the organic thin layer comprises at least a light-emitting layer, and may further comprise a hole-injecting layer, hole-transporting layer, hole-blocking layer, electron-transporting layer, electron-injecting layer, and the like according to necessity. The light-emitting layer may be formed so as to function as a light-emitting layer alone or may be formed as a multifunctional layer such as a light-emitting and electron-transporting layer and light-emitting and hole-transporting layer.

-Light-Emitting Layer-

The light-emitting layer is not particularly limited and may be properly selected depending on the application, but preferably comprises, for example, the organometallic complex of the invention as a light-emitting material. In this case, the light-emitting layer may be formed by applying the organometallic complex alone. Alternatively, the light-emitting layer may be formed such that it contains, other material in addition to the organometallic complex, for example, in addition to the organometallic complex of the invention as a guest material, a host material capable of emitting light with a wavelength near to the absorption wavelength of the guest material. Preferably, the host material is contained in the light-emitting layer; or the host material may be contained in the hole-transporting layer, electron-transporting layer, or the like.

In the case where the organometallic complex of the invention as the guest material and the host material are used in combination, the host material is initially excited when EL emission is generated. Since the emission wavelength of the host material and the absorption wavelength of the guest material (the organometallic complex) overlap, excitation energy is efficiently transferred from the host material to the guest material, and since the host material returns to the ground state without emitting light and only the guest material which is in an excited state emits excitation energy as light, the emission efficiency and color purity are excellent.

In general, when only one species of luminescent molecules is present or the molecules are contained at high concentration in a thin film, the luminescent molecules are so close to each other that they interact, and a so-called "concentration quenching" effect occurs in which the emission efficiency declines. However, when the guest material and host material are used together, the organometallic complex as the guest compound is dispersed at relatively low concentration in the host compound, so the "concentration quenching" effect is effectively suppressed and excellent emission efficiency is obtained. The use of the two materials in combination is therefore advantageous. Moreover, by using the guest material together with the host material in the light-emitting layer, as the host material generally has excellent film-forming properties, the combination has excellent film-forming properties while maintaining luminescent properties.

The host material is not particularly limited and may be properly selected depending on the application; preferably, the emission wavelength of the host material is near to the absorption wavelength of the guest material. Suitable examples of the host material include aromatic amine derivatives expressed by the following structural formula (63), carbazole derivatives expressed by the following structural formula (64), oxine complexes expressed by the following structural formula (65), 1,3,6,8-tetraphenylpyrene compounds expressed by the following structural formula (66), 4,4'-bis(2,2'-diphenylvinyl)-1,1'-biphenyl (DPVBi) expressed by the following structural formula (67) (main emission wavelength=470 nm), p-sexiphenyl expressed by the following structural formula (68) (main emission wavelength=400 nm), 9,9'-bianthryl expressed by the following structural formula (69) (main emission wavelength=460 nm), polymer materials which will be described later, and the like.

structural formula (63)

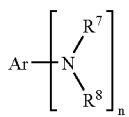

In the structural formula (63), "n" is an integer of 2 or 3, Ar is a divalent or trivalent aromatic group or a heterocyclic aromatic group, $R^7$ and $R^8$ may be identical or different, and are a monovalent aromatic group or heterocyclic aromatic group. The monovalent aromatic group or heterocyclic aromatic group is not particularly limited and may be properly selected depending on the application.

Among the aromatic amine derivatives expressed by the structural formula (63), N,N'-dinaphthyl-N,N'-diphenyl-[1,1'-biphenyl]-4,4'-diamine (NPD) expressed by the following structural formula (70) (main emission wavelength=430 nm) and its derivatives are preferable.

structural formula (70)

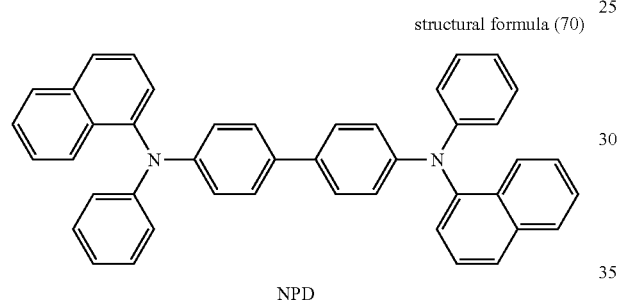

NPD structural formula (64)

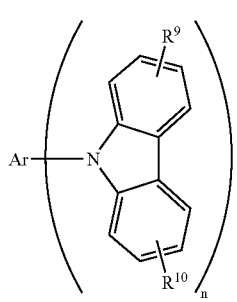

In the structural formula (64), Ar is a divalent or trivalent group containing an aromatic ring as shown below, or a divalent or trivalent group containing a heterocyclic aromatic ring.

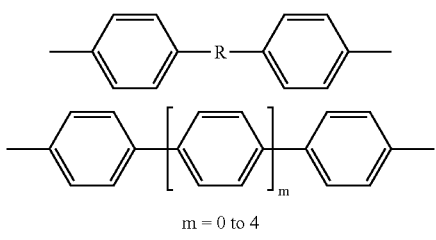

m = 0 to 4

-continued

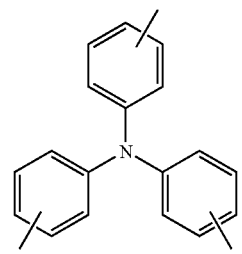

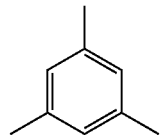

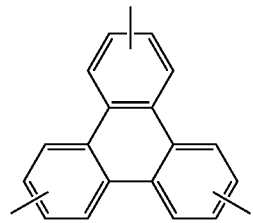

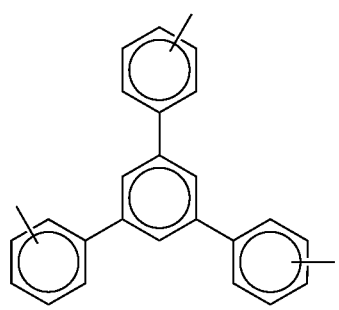

These may be substituted by a non-conjugated group and R represents a crosslinking group; suitable examples thereof are shown below.

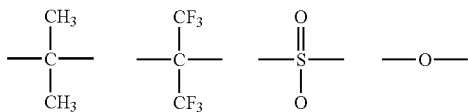

In the structural formula (64), $R^9$ and $R^{10}$ represent independently a hydrogen atom, halogen atom, alkyl group, aralkyl group, alkenyl group, aryl group, cyano group, amino group, acyl group, alkoxy carbonyl group, carboxyl group, alkoxy group, alkyl sulfonyl group, hydroxyl group, amide group, aryloxy group, aromatic hydrocarbon ring or aromatic heterocyclic groups, and these may be further substituted by a substituent group.

In the structural formula (64), n represents an integer, and 2 and 3 are preferable.

Among the carbazole derivatives expressed by the structural formula (64), those are preferable that are selected from the compound in which Ar is an aromatic group such that two benzene rings are connected via a single bond, $R^9$ and $R^{10}$ are each a hydrogen atom, and n=2, i.e., 4,4'-bis(9-carbazolyl)-biphenyl (CBP) expressed by the following structural formula (71) (main emission wavelength=380 nm) and its derivatives, in terms of particularly excellent efficiency, and the like.

structural formula (71)

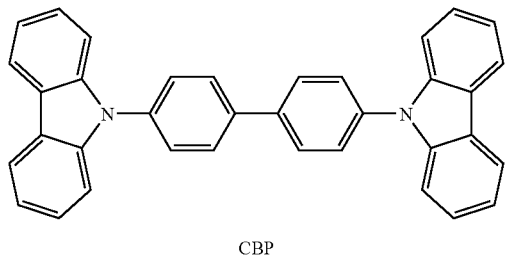

CBP structural formula (65)

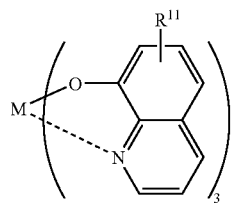

In the structural formula (65), $R^{11}$ represents a hydrogen atom, halogen atoms, alkyl group, aralkyl group, alkenyl group, aryl group, cyano group, amino group, acyl group, alkoxy carbonyl group, carboxyl group, alkoxy group, alkyl sulfonyl group, hydroxyl group, amide group, aryloxy group, aromatic hydrocarbon ring or aromatic heterocyclic group, and these may be further substituted by a substituent group.

Among oxine complexes represented by the structural formula (65), the aluminum quinoline complex (Alq) expressed by the following formula (72) (main emission wavelength=530 nm) is preferable.

structural formula (72)

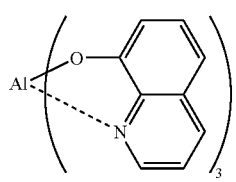

Alq structural formula (66)

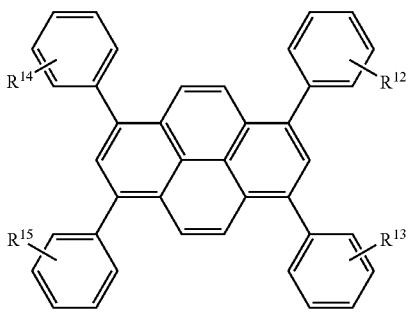

In the structural formula (66), $R^{12}$ to $R^{15}$ may be identical or different, and represent a hydrogen atom or substituent group respectively. Suitable examples of the substituent group include alkyl groups, cycloalkyl groups, or aryl groups for example, and these may be further substituted by a substituent group.

Among the 1,3,6,8-tetraphenylpyrenes represented by the structural formula (66), the compound in which $R^{12}$ to $R^{15}$ are hydrogen atoms, i.e., the 1,3,6,8-tetraphenylpyrene expressed by the following structural formula (73) (main emission wavelength=440 nm) is preferable from the viewpoint of excellent emission efficiency, and the like.

structural formula (73)

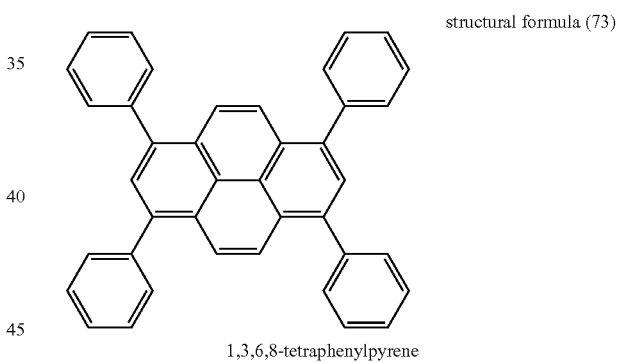

1,3,6,8-tetraphenylpyrene structural formula (67)

structural formula (68)

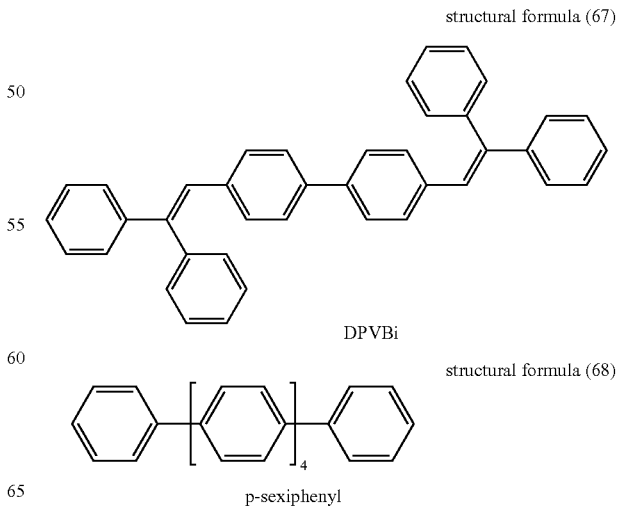

DPVBi p-sexiphenyl

-continued structural formula (69)

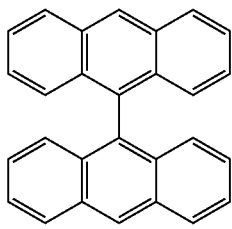

9,9′-bianthryl

The polymer material as the host material is not particularly limited and may be properly selected depending on the application, but, for example, it is preferable that the polymer material is selected from polyparaphenylenevinylenes (PPV), polythiophenes (PAT), polyparaphenylenes (PPP), polyvinylcarbazols (PVCz), polyfluorenes (PF), polyacetylenes (PA), and derivatives thereof, which are expressed by the following structural formulae.

PPV derivatives

PAT derivatives

PPP derivatives

PVCz derivatives

PF derivatives

PA derivatives

In the structural formulae, R represents one of a hydrogen atom, halogen atom, alkoxy group, amino group, alkyl group, cycloalkyl groups, aryl group that may contain a nitrogen atom or sulfur atom, or aryloxy groups; and these may be further substituted by a substituent group. x represents an integer.

Among the polymer materials as the host material, polyvinylcarbazols (PVCz) expressed by the structural formula (70) are preferable in that energy is efficiently transferred from a host to a guest.

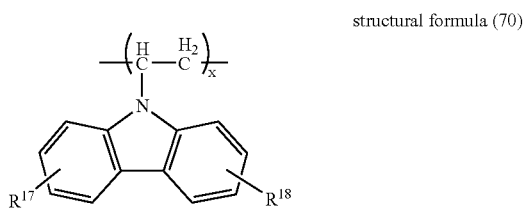

structural formula (70)

In the structural formula (70), $R^{17}$ and $R^{18}$ represent respectively plural substituent groups attached to any sites of cyclic structure. $R^{17}$ and $R^{18}$ represent independently a halogen atom, alkoxy group, amino group, alkyl group, cycloalkyl group, aryl group that may contain a nitrogen atom or sulfur atom, or aryloxy group; and these may be substituted by a substituent group. Any of adjoining substituted positions of the $R^{17}$ and $R^{18}$ may connect each other to form a ring that may contain a nitrogen, sulfur, or oxygen atom; and these may be substituted by a substituent group; "x" represents an integer.

When the polymer material is used as a host material, the host material is dissolved in a solvent, and the organometallic complex of the invention as the guest material is mixed to prepare a coating solution. Then, the coating solution can be applied by wet film forming methods such as a spin coating method, ink-jet method, dip coating method, and blade coating method. At this time, in order to improve electron transport property of the layer to be formed by application, a material for hole-transporting layer and a material for electron-transporting layer may be mixed simultaneously in a solvent to form a film on the layer. These wet film forming methods is suitable especially when a multifunctional light-emitting layer is formed as a single layer (hole-transporting, electron-transporting, and light-emitting layer).

The containing layer of the organometallic complex in the light-emitting layer is not particularly limited, may be properly selected depending on the application, and for example, is preferably 0.1% by mass to 50% by mass, more preferably 0.5% by mass to 20% by mass.

When the content is less than 0.1% by mass, life time, light emitting efficiency, etc. may be insufficient. When the content is 50% by mass or more, color purity may be deteriorated. In contraset, the content within the more preferable range is advantageous for excellent life time and emission efficiency.

The ratio of the organometallic complex of the invention as the guest material and the host material (molar ratio, guest material: host material) in the light-emitting layer is preferably from 1:99 to 50:50 and more preferably from 1:99 to 10:90.

When the light-emitting layer is formed as a multifunctional layer such as a light emitting and electron-transporting layer, and light-emitting and hole-transporting layer, the content of the organometallic complex in these layers can be set to the same range as described above.

The light-emitting layer can inject a hole from the positive electrode, hole-injecting layer, the hole-transporting layer, or the like upon application of an electric field, can inject an electron from the negative electrode, electron-injecting layer, the electron-transporting layer, or the like, and further provides the place where the hole and the electron are recombined The light-emitting layer may inject holes from the positive electrode, hole injecting layer, the hole-transporting layer, or the like when an electric field is applied, and also may inject electrons from the negative electrode, electron-injecting layer, the electron-transporting layer, or the like; thus, the light-emitting layer may provide a field of recombination between the holes and the electrons and may enable the organometallic complex (light-emitting material and luminescent molecules) exhibiting emission, to emit light by the action of recombination energy generated by the recombination. The light-emitting layer may further comprise other light-emitting materials in addition to the organometallic complex within a range not deteriorating the emission.

The light-emitting layer may be properly produced by conventional methods such as a vapor deposition method, wet film forming method, MBE (molecular beam epitaxial) method, cluster ion beam method, molecule laminating method, LB method, printing method, transfer method, and the like.

Among them, vapor deposition method is typically proper, since organic solvents are not used and thus is free from the waste products of the solvents, the cost is lower, and the production efficiency is higher. By the way, wet film forming method is also preferable when the light-emitting layer is of single layer configuration such as a hole-transporting, light-emitting, and electron-transporting layer.

The vapor deposition method is not particularly limited and may be properly selected from known methods depending on the application. Examples thereof include a vacuum vapor deposition, resistance heating vapor deposition, chemical vapor deposition, physical vapor deposition, and the like. Examples of chemical vapor deposition include plasma CVD, laser CVD, heat CVD, gas source CVD, and the like. The light-emitting layer can be suitably formed by means of the vapor deposition through subjecting the organometallic complex to vacuum vapor deposition, for example. When the light-emitting layer comprises the host material in addition to the organometallic complex, the organometallic complex and the host material are subjected to simultaneous vacuum vapor deposition. In the former case, production is easy in that co-vapor deposition is not required.

The wet film forming method is not particularly limited and may be properly selected from known methods depending on the application. Examples thereof include an ink-jet method, spin coating method, kneader coating method, bar coating method, blade coating method, casting method, dipping method, curtain coating method, and the like.

In the wet film forming method, a solution may be used or applied into which the material of the light-emitting layer is dissolved or dispersed together with a resin component. Examples of the resin component include polyvinyl carbazoles, polycarbonates, polyvinyl chlorides, polystyrenes, polymethyl methacrylates, polyesters, polysulfones, polyphenylene oxides, polybutadiene, hydrocarbon resins, ketone resins, phenoxy resins, polyamides, ethyl cellulose, vinyl acetate, acrylonitrile butadiene styrene (ABS) resins, polyurethane, melamine resins, unsaturated polyester resins, alkyd resins, epoxy resins, and silicone resins.

The light-emitting layer may be suitably prepared by the wet film forming method, for example, by means of a solution of coating composition that contains the organometallic complex and the optional resin material in a solvent, by applying and drying the coating composition. When the light-emitting layer comprises the host material in addition to the organometallic complex, the light-emitting layer may be prepared from a solution of coating composition that comprises the organometallic complex, the host material, and the optional resin material dissolved in a solvent, by applying and drying the coating composition.

The thickness of the light-emitting layer is not particularly limited, may be properly selected depending on the application, and is, for example, preferably 1 nm to 50 nm, more preferably 3 nm to 20 nm.

The light-emitting layer having a thickness within the preferable range may lead to sufficient emission efficiency, emission luminance, and color purity emitted by the organic EL element. The light-emitting layer having a thickness within the more preferable range is advantageous in that those are more remarkable.

-Positive Electrode-

The positive electrode is not particularly limited and may be properly selected depending on the application. Preferably, the positive electrode supplies holes or carriers to the organic thin layer. Specifically, the positive electrode is preferably capable of supplying carriers to the light-emitting layer when the organic thin layer comprises the light-emitting layer alone, to the hole-transporting layer when the organic thin layer further comprises the hole-transporting layer, and to the hole-injecting layer when the organic thin layer further comprises the hole-injecting layer.

The material of the positive electrode is not particularly limited and may be properly selected depending on the application from metals, alloys, metal oxides, electrically conducting compounds, mixtures thereof and the like, for example. Among these, materials having a work function of 4 eV or more are preferable.

Specific examples of the material of the positive electrode include electrically conducting metal oxides such as tin oxide, zinc oxide, indium oxide, and indium tin oxide (ITO), metals such as gold, silver, chromium, and nickel, mixtures or laminates of these metals and electrically conducting metal oxides, inorganic electrically conducting substances such as copper iodide and copper sulfide, organic electrically conducting materials such as polyaniline, polythiophene and polypyrrole, and laminates of these with ITO. These may be used singly or in combination. Among these, electrically conducting metal oxides are preferable, and ITO is particularly preferable from the viewpoints of productivity, high conductivity, and transparency.

The thickness of the positive electrode is not particularly limited and may be properly selected depending on the material etc.; preferably the thickness is 1 nm to 5,000 nm, more preferably is 20 nm to 200 nm.

The positive electrode is typically formed on a substrate of glass such as soda lime glass and non-alkali glass, or transparent resin.

When the glass is employed as the substrate, non-alkali glass or soda lime glass with a barrier layer of silica or the like is preferable from the viewpoint suppressing the elution of ions from the glass.

The thickness of the substrate is not particularly limited provided that the mechanical strength is sufficient. When a glass is employed as the substrate, the thickness is typically 0.2 mm or more, preferably is 0.7 mm or more.

The positive electrode may be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, transfer method, and method of applying a dispersion of the ITO by chemical reaction method (sol-gel process etc.).

By washing the positive electrode and performing other treatment, the driving voltage of the organic EL element may be reduced, and the emission efficiency may also be increased. Suitable examples of other treatment include UV ozonization, plasma processing and the like, when the material of the positive electrode is ITO.

-Negative Electrode-

The negative electrode is not particularly limited and may be properly selected depending on the application. Preferably, the negative electrode supplies electrons to the organic thin layer. Specifically, the negative electrode is preferably capable of supplying electrons to the light-emitting layer when the organic thin layer comprises the light-emitting layer alone, to the electron-transporting layer when the organic thin layer further comprises the electron-transporting layer, and to the electron-injecting layer when the organic thin layer further comprises the electron-injecting layer.

The material of the negative electrode is not particularly limited and may be properly selected depending on the adhesion properties with the layers or molecules adjoining the negative electrode, such as the electron-transporting layer and light-emitting layer, and according to ionization potential, stability and the like. Examples thereof include a metal, alloy, metal oxide, electrically conducting compound, and mixture thereof.

Specific examples of the material of the negative electrode include alkali metals such as Li, Na, K, and Cs; alkaline earth metals such as Mg and Ca; gold, silver, lead, aluminum, sodium-potassium alloys or mixed metals thereof, lithium-aluminum alloys or mixed metals thereof, magnesium-silver alloys or mixed metals thereof; rare earth metals such as indium and ytterbium; and alloys of these metals.

These may be used singly or in combination. Among these, materials having a work function of 4 eV or less are preferable. Aluminum, lithium-aluminum alloy or mixed metals thereof, magnesium-silver alloy, or mixed metals thereof, or the like are more preferable.

The thickness of the negative electrode is not particularly limited and may be properly selected depending on the material of the negative electrode and the like; preferably the thickness is 1 nm to 10,000 nm, more preferably is 20 nm to 200 nm.

The negative electrode can be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, and transfer method.

When two or more materials are used together as the material of the negative electrode, the materials may be vapor-deposited simultaneously to form an alloy electrode or the like, or a pre-prepared alloy may be vapor-deposited to form an alloy electrode or the like.

Preferably, the resistances of the positive electrode and negative electrode are lower, and are below several hundreds ohm/square.

-Hole-Injecting Layer-

The hole-injecting layer is not particularly limited and may be properly selected depending on the application; preferably, the hole-injecting layer is capable of injecting holes from the positive electrode when an electric field is applied.

The material for the hole-injecting layer is not particularly limited and may be properly selected depending on the application; and suitable examples of the material include starburst amine [4,4',4''-tri(2-naphthylphenylamino)triphenylamine] expressed by the following structural formula (74) (hereinafter, may be abbreviated as "2-TNATA"), copper phthalocyanine, and polyanilines.

structural formula (74)

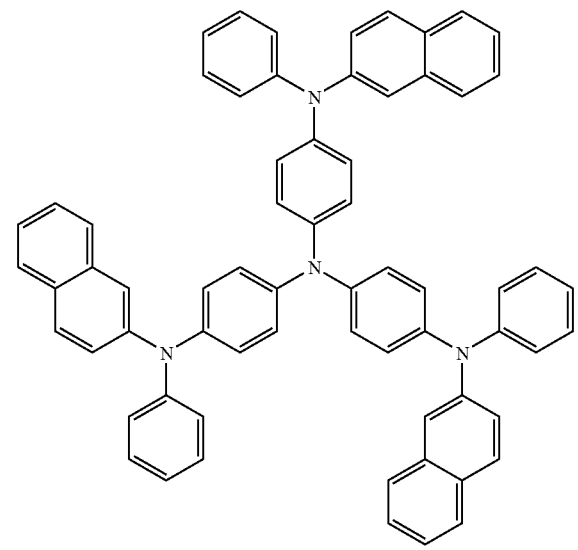

The thickness of the hole-injecting layer is not particularly limited and may be properly selected depending on the application; preferably, the thickness is about 1 nm to about 100 nm, and more preferably is 5 nm to 50 nm.

The hole-injecting layer can be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, and transfer method.

-Hole-Transporting Layer-

The hole-transporting layer is not particularly limited and may be properly selected depending on the application; preferably, the hole-transporting layer is capable of transporting holes from the positive electrode when an electric field is applied.

The material of the hole-transporting layer is not particularly limited and may be properly selected depending on the application; examples thereof include aromatic amine compounds, carbazole, imidazole, triazole, oxazole, oxadiazole, polyarylalkane, pyrazoline, pyrazolone, phenylene diamine, arylamine, amino-substituted chalcone, styryl anthracene, fluorenone, hydrazone, stilbene, silazane, styryl amine, aromatic dimethylidene compounds, porphyrin compounds, electrically conducting high-molecular oligomers and polymers such as polysilane compounds, poly(N-vinyl carbazole), aniline copolymers, thiophene oligomers and polymers, and polythiophene, and carbon films. When one of these materials for hole-transporting layer is mixed with a material for the light-emitting layer to form a film, a hole-transporting and light-emitting layer can be formed.

These materials of the hole-transporting layer may be used singly or in combination. Among these, aromatic amine compounds are preferable, and specifically, TPD (N,N'-diphenyl-N,N'-bis(3-methylphenyl)-[1,1'-biphenyl]-4,4'-diamine) expressed by the following structural formula (75), and NPD (N,N'-dinaphthyl-N,N'-diphenyl-[1,1'-biphenyl]4,4'-diamine) expressed by the following structural formula (76), and the like are more preferable.

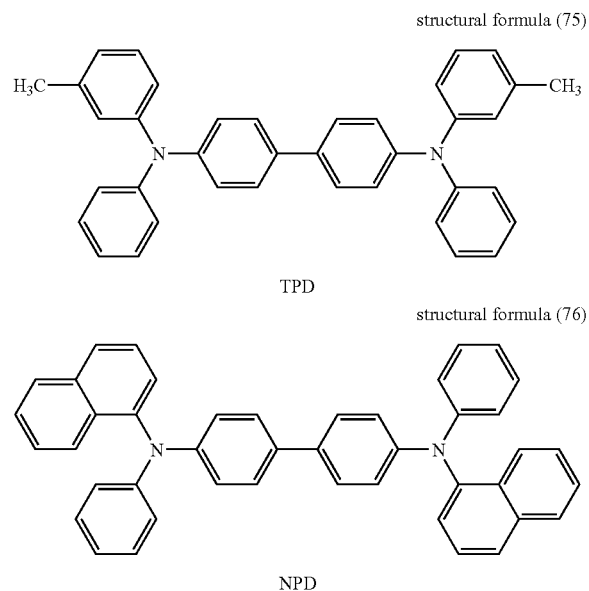

structural formula (75)

TPD structural formula (76)

NPD

The thickness of the hole-transporting layer is not particularly limited and may be properly selected depending on the application; usually the thickness is 1 nm to 500 nm, and preferably is 10 nm to 100 nm.

The hole-transporting layer may be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, and transfer method.

-Hole Blocking Layer-

The hole-blocking layer is not particularly limited and may be properly selected depending on the application; such a layer is preferable that may perform to barrier the holes injected from the positive electrode.

The material of the hole-blocking layer is not particularly limited and may be properly selected depending on the application.

When the organic EL element comprises the hole-blocking layer, holes transported from the positive electrode are blocked by the hole-blocking layer, and electrons transported from the negative electrode pass through the hole-blocking layer and arrive at the light-emitting layer. Hence, recombination of electrons and holes occurs efficiently in the light-emitting layer, and recombination of the holes and electrons in the organic thin layer other than the light-emitting layer can be prevented. Thus, the luminescence from a light-emitting material, which is intended, is obtained efficiently, and this is advantageous in respect of color purity.

The hole-blocking layer is preferably disposed between the light-emitting layer and the electron-transporting layer.

The thickness of the hole-blocking layer is not particularly limited and may be properly selected depending on theapplication; for example, usually the thickness is about 1 nm to about 500 nm, and preferably is 10 nm to 50 nm. The hole-blocking layer may be of single layer or multilayered configuration.

The hole-blocking layer may be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, or transfer method.

-Electron-Transporting Layer-

The electron-transporting layer is not particularly limited and may be properly selected depending on the application; for example, such a layer is preferable that performs to transport electrons from the negative electrode, or to act as a barrier to holes injected from the positive electrode.

The material of the electron-transporting layer is not particularly limited and may be properly selected depending on the application; examples thereof include quinoline derivatives such as the aluminum quinoline complexes (Alq), oxadiazole derivatives, triazole derivatives, phenanthroline derivatives, perylene derivatives, pyridine derivatives, pyrimidine derivatives, quinoxaline derivatives, diphenylquinone derivatives and nitro-substituted fluorene derivatives. When one of these materials for electron-transporting layer is mixed with a material for the light-emitting layer to form a film, an electron-transporting and light-emitting layer can be formed, and when a material for the hole-transporting layer is also mixed to form a film, an electron-transporting, hole-transporting and light-emitting layer can be formed. In this case, a polymer such as polyvinyl carbazole or polycarbonate can be used.

The thickness of the electron-transporting layer is not particularly limited and may be properly selected depending on the application; for example, usually the thickness is about 1 nm to about 500 nm, and preferably is 10 nm to 50 nm.

The electron-transporting layer may be of single layer or multilayered configuration.

In this case, it is preferable that an electron-transporting material used for the electron-transporting layer adjacent to the light-emitting layer has an optical absorption edge at a shorter wavelength than that of the organometallic complex so that it limits the luminescence region in the organic EL element to the light-emitting layer and prevents unwanted luminescence from the electron-transporting layer. Examples of the electron-transporting material, which has an optical absorption edge at a shorter wavelength than that of the organometallic complex, include phenanthroline derivatives, oxadiazole derivatives and triazole derivatives; suitable examples include 2,9-dimethyl-4,7-diphenyl-1,10-phenanthroline (BCP) expressed by the following structural formula (77) and the compounds shown in the following structural formulae (78) to (80).

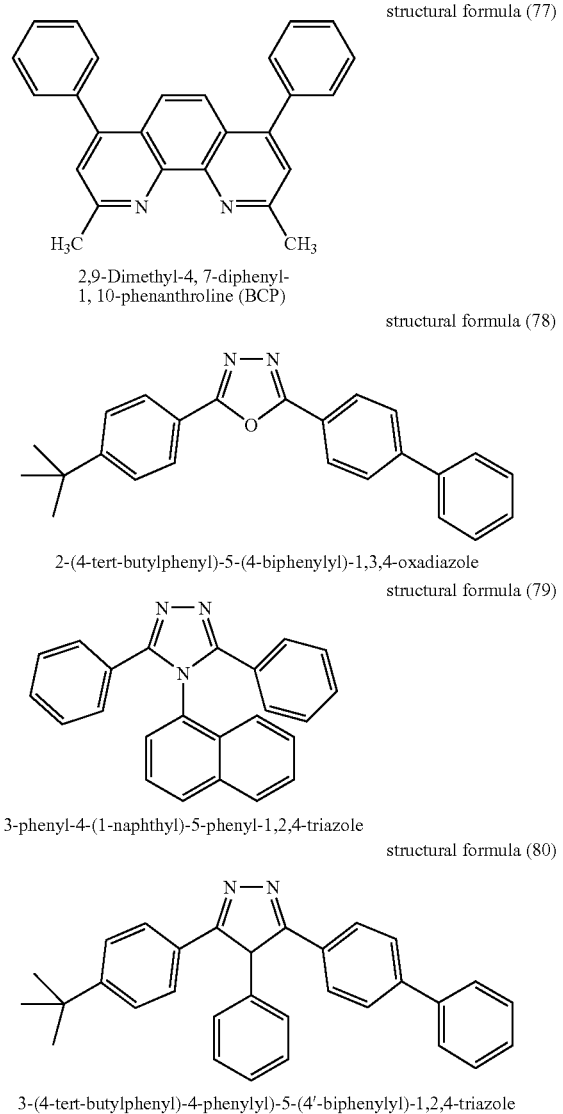

structural formula (77)
2,9-Dimethyl-4, 7-diphenyl-1, 10-phenanthroline (BCP)

structural formula (78)
2-(4-tert-butylphenyl)-5-(4-biphenylyl)-1,3,4-oxadiazole structural formula (79)
3-phenyl-4-(1-naphthyl)-5-phenyl-1,2,4-triazole structural formula (80)
3-(4-tert-butylphenyl)-4-phenylyl)-5-(4'-biphenylyl)-1,2,4-triazole The electron-transporting layer can be suitably formed by the above-mentioned methods such as a vapor deposition method, wet film forming method, electron beam method, sputtering method, reactive sputtering method, molecular beam epitaxy (MBE) method, cluster ion beam method, ion plating method, plasma polymerization method (high frequency excitation ion plating method), molecule laminating method, LB method, printing method, or transfer method.

-Electron-Injecting Layer-

The material of the electron-injecting layer is not particularly limited and may be properly selected depending on the application; for example, alkaline metal fluoride such as lithium fluoride, alkaline earth metal fluoride such as strontium fluoride, and the like are suitably used. The thickness of the electron-injecting layer is not particularly limited and may be properly selected depending on the application; for example, the thickness is usually about 0.1 nm to about 10 nm, preferably is 0.5 nm to 2 nm.

The electron-injecting layer may be suitably formed by, for example, a vapor deposition method, electron beam method, sputtering method, or the like.

-Other Layers-

The organic EL element of the invention may have other layers properly selected depending on the application. Suitable examples of the other layer include a color conversion layer and protective layer, and the like.

-Color Conversion Layer-

Preferably, the color conversion layer comprises a phosphorescent material and more preferably comprises the organometallic complex of the invention. The color conversion layer may be formed of the organometallic complex alone and may further comprise other materials.

In the color conversion layer, the organometallic complexes may be used singly or in combination.

By the way, it is generally known that the wavelength of excitation light is not the same as that of emission light because the organic molecule excited by light with a certain wavelength loses part of the excitation energy nonradiatively as heat energy or the like due to the interaction within the molecule or with other molecules before the excited organic molecule emits light to transit from an excited state to a ground state. The energy difference between the excitation light and emission light is called stokes shift. As a color converting material for use in the color conversion layer, a fluorescent material, from which only emission from singlet is seen, has been used because the material can be selected from a wide range of materials. However, the fluorescent material has a small stokes shift (<100 nm) and emission is seen in the longer wavelength region adjacent to the strongest absorption band present in the visible range. Thus, for example, blue-line emission cannot be efficiently absorbed to be converted into red-line color. On the other hand, the organometallic complex of the invention is a phosphorescent material. Thus, when a singlet excited state is generated as a result of excitation by light with a certain wavelength, the organometallic complex of the invention can transit quickly to a triplet excited state, which is lower energy state than the singlet excited state, to emit phosphorescence. Thus, the stokes shift becomes large (It is known that in the case of normal organic matter, triplet state is 0.1 eV to 2 eV lower in energy than singlet excited state). For example, in the application of converting blue-line emission serving as excitation source into red color, the color conversion layer using a phosphorescent material has a higher rate of absorption of blue light compared to the case where a fluorescent material is used, thus leading to higher rate of color conversion per molecule. In other words, since the color conversion layer where the fluorescent material is used absorbs less blue light, more blue light passes through the color conversion layer. In order to compensate this, by making the color conversion layer thick without changing dispersion concentration, the absorption amount of blue light increases, enabling the amount of red light to increase. However, in the manufactured organic EL element, exudations from the color conversion layer, such as moisture or organic solvent residues, causes deterioration of materials constituting an organic EL element and region where light is not emitted is generated, which is a big problem. Thus, it is better to make the color conversion layer as thin as possible. Further, in the color conversion layer using a fluorescent material, low rate of absorption of a guest is compensated by using a host which absorbs blue light in combination. However, when the phosphorescent material is used, materials serving as a host are not always required to be used in combination, and even when used alone, high color conversion efficiency can be obtained. Thus, the color conversion layer using a phosphorescence material is advantageous in that many problems can be solved simultaneously such as light emission from the host molecule, deterioration of properties of manufactured color conversion layer, and increase of production cost of a substrate, which are concerned when the color conversion layer is prepared by using a host in combination. In addition, considering the case where the host is used, when the concentration of the fluorescent material is too high, as mentioned above, concentration quenching effect occurs, frequently resulting in remarkable decrease of light emission, however; it is known that the phosphorescent material doesn't tend to cause concentration quenching compared to the fluorescent material, and the concentration at which the phosphorescent material is dispersed is not restricted. For example, more phosphorescent materials emit light even in a powder state compared with fluorescent materials, and conversely, when the concentration at which the phosphorescent material is dispersed is too low, light emission is weakened due to quenching effect by oxygen molecules. The use of phosphorescent material in a powder state is useful in that suppression of the deterioration of the color conversion layer can be achieved. Since the color conversion layer is always exposed to light in a photolithography step and ITO patterning step at the stage of preparing a substrate, and in the process of carrying out color conversion as an element, there is a problem that color conversion efficiency is reduced due to light deterioration. When light-emitting material dispersed in the color conversion layer is used, the light-emitting material is exposed to light individually and thus is deteriorated rapidly, which is extremely difficult to prevent. In contrast, in the color conversion layer where phosphorescent material in a powder state is used, the phosphorescent material is exposed to light in bulk. Thus, such a color conversion layer can be obtained that the deterioration is suppressed, life time is long, and conversion efficiency does not vary.

The color conversion layer can be arranged at any position without limitation and the position may be properly selected depending on the application. For example, when full color display is conducted, the color conversion layer is preferably arranged on a pixel.

In the organic EL element of the invention, preferably, the color conversion layer can convert incident light into light with wavelength longer by 100-nm or more than that of the light, and more preferably, the color conversion layer can convert incident light into light with wavelength longer by 150 nm or more than that of the light.

Moreover, such a color conversion layer is preferable that may convert light with a wavelength region from ultraviolet light to blue light into red light.

The color conversion layer can be formed by any method without limitation and the method may be properly selected depending on the application. Suitable examples thereof include a vapor deposition method, coating method, and the like.

In the invention, known color filters may be used as the color conversion layer.

-Protective Layer-

The protective layer is not particularly limited and may be properly selected depending on the application; for example, such a layer is preferable that can prevent molecules or substances as moisture or oxygen which promote deterioration of the organic EL element, from penetrating into the organic EL element.

Examples of the material of the protective layer include metals such as In, Sn, Pb, Au, Cu, Ag, Al, Ti and Ni; metal oxides such as MgO, SiO, $SiO_2$, $Al_2O_3$, GeO, NiO, CaO, BaO, $Fe_2O_3$, $Y_2O_3$ and $TiO_2$; nitrides such as SiN and SiNxOy; metal fluorides such as $MgF_2$, LiF, $AlF_3$, $CaF_2$; polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, copolymer obtained by copolymerizing a monomer mixture comprising tetrafluoroethylene and at least one comonomer, fluorine-containing copolymer having a ring structure in a main chain of the copolymer, water-absorbing substance having a water absorption rate of 1% or more, and damp-proof substance having a water absorption rate of 0.1% or less.

The protective layer may be suitably formed by, for example, the above-mentioned methods such as a vapor deposition method, wet film forming method, sputtering method, reactive sputtering method, molecular beam epitaxy (MBE) method, cluster ion beam method, ion plating method, plasma polymerization method (high frequency excitation ion plating method), printing method, and transfer method.

-Layer Configuration-

The layer configuration of the organic EL element of the invention is not particularly limited and may be properly selected depending on the application; suitable examples thereof include the following layer configurations (1) to (13):

(1) Positive electrode/hole-injecting layer/hole-transporting layer/light-emitting layer/electron-transporting layer/electron-injecting layer/negative electrode, (2) Positive electrode/hole-injecting layer/hole-transporting layer/light-emitting layer/electron-transporting layer/negative electrode, (3) Positive electrode/hole-transporting layer/light-emitting layer/electron-transporting layer/electron-injecting layer/negative electrode, (4) Positive electrode/hole-transporting layer/light-emitting layer/electron-transporting layer/negative electrode, (5) Positive electrode/hole-injecting layer/hole-transporting layer/light-emitting and electron-transporting layer/electron-injecting layer/negative electrode (6) Positive electrode/hole-injecting layer/hole-transporting layer/light-emitting and electron-transporting layer/negative electrode, (7) Positive electrode/hole-transporting layer/light-emitting and electron-transporting layer/electron-injecting layer/negative electrode, (8) Positive electrode/hole-transporting layer/light-emitting and electron-transporting layer/negative electrode, (9) Positive electrode/hole-injecting layer/hole-transport and light-emitting layer/electron-transporting layer/electron-injecting layer/negative electrode

(10) Positive electrode/hole-injecting layer/hole-transport and light-emitting layer/electron-transporting layer/negative electrode,

(11) Positive electrode/hole-transport and light-emitting layer/electron-transporting layer/electron-injecting layer/negative electrode,

(12) Positive electrode/hole-transporting and light-emitting layer/electron-transporting layer/negative electrode,

(13) Positive electrode/hole-transport, light-emitting and electron-transporting layer/negative electrode.

When the organic EL element comprises the hole-blocking layer, the hole-blocking layer is preferably arranged between the light-emitting layer and the electron-transporting layer in the layer configurations (1) to (13).

Among these layer configurations, the aspect (4) of positive electrode/hole-transporting layer/light-emitting layer/electron-transporting layer/negative electrode is shown in FIG. 1. Organic EL element 10 has a layer configuration comprising positive electrode 14 (e.g. ITO electrode) formed on glass substrate 12, hole-transporting layer 16, light-emitting layer 18, electron-transporting layer 20, and negative electrode 22 (e.g. Al—Li electrode) laminated in this order. Positive electrode 14 (e.g. ITO electrode) and negative electrode 22 (e.g. Al—Li electrode) are interconnected through a power supply. Organic thin layer 24 is formed by hole-transporting layer 16, light-emitting layer 18, and electron-transporting layer 20.

The longer the luminance half-life period of the organic EL element of the invention is, the more preferable. For example, in the continuous operation at a current density of 50 A/m$^2$, the period is preferably 5 hours or more, more preferably 20 hours or more, further preferably 40 hours or more, and particularly preferably 60 hours or more.

The peak emission wavelength of the organic EL element of the invention is not particularly limited and may be properly selected from visible light region; for example, the wavelength is preferably 400 nm to 650 nm As the emission voltage of the organic EL element of the invention, the organic EL element emits light desirably at a voltage of 10 V or less, preferably 8 V or less, and more preferably 7 V or less.

The current efficiency of the organic EL element of the invention at a current density of 5 A/m$^2$ is preferably 10 cd/A or more, more preferably 30 cd/A or more, and still more preferably 40 cd/A or more.

-Application or the Like-

The organic EL elements of the invention may be appropriately utilized in a variety of regions such as computers, on-vehicle displays, outdoor displays, household appliances, commercial equipment, household equipment, traffic displays, clock displays, calendar displays, luminescent screens, and audio equipment; in addition, may be preferably utilized for lighting apparatuses and the following organic EL displays of the invention.

(Organic EL Display)

The organic EL display of the invention is not particularly limited, and the construction may be conventional, provided that the organic EL element of the invention is included.

The organic EL display may be a monochrome, multicolor, or full color type.

With respect to methods for providing the full-color organic EL display, the representative methods are, as illustrated in "Monthly Display, September 2000 issue, pages 33-37", three-color light emitting methods in which organic EL elements each emitting light corresponding to the three primary colors, red (R), green (G), or blue (B) light, are disposed on a substrate; white color methods in which white light from a white light emitting organic EL element is separated into three primary colors through a color filter; and color conversion methods in which blue light from a blue light emitting organic EL element is converted into red (R) and green (G) colors through a fluorescent dye layer. In the invention, as the organic EL element of the invention emits red light, the three-color light emitting methods, color conversion methods, or the like can be suitably used.

When the organometallic complex of the invention is used as a color conversion material, the color conversion methods are particularly suitably employed.

Figure 2:
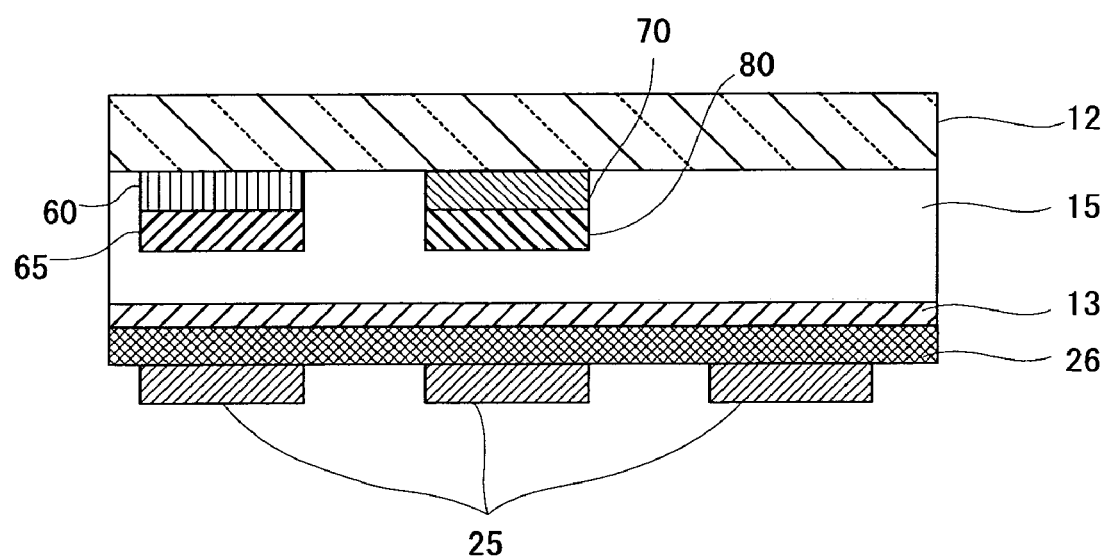
FIG. 2 is a schematic view showing an exemplary configuration of an organic EL display comprising a color conversion layer.

FIG. 2 shows a specific example of the organic EL display of the invention according to the color conversion method. This organic EL display comprises electrodes 25 disposed corresponding to a pixel; organic thin layer 26 for emitting blue light arranged over the electrodes; and transparent electrode 13 further thereon. In addition, a laminate of color conversion layer 60 for red color and red color filter 65, and a laminate of color conversion layer 70 for green color and green color filter 80 are disposed on the transparent electrode 13 via protective layer (planarizing layer) 15. Further, glass substrate 12 is arranged over these.

When a voltage is applied between electrodes 25 and transparent electrode 13 in this organic EL display, organic thin layer 26 for emitting blue light emits blue light. Part of this blue light emission passes through transparent electrode 14, further passes through protective layer 15 and glass substrate 10 without conversion, and is radiated to the outside. On the other hand, in the region where color conversion layer 60 for red color and color conversion layer 70 for green color, the blue light emission is converted into red or green colors in each of these color conversion layers, and further passes through red color filter 65 or green color filter 80, by which the blue light emission turns into red light emission or green light emission and passes through glass substrate 12. As a result, the organic EL display can display full color.

When color conversion layers 60 and 70 are formed of the organometallic complex of the invention (phosphorescent material), even the color conversion layer for red color can be formed as a film of the organometallic complex alone without using a host material, etc, which makes the production easy and besides, the resulting color conversion layers have extraordinary excellent color conversion efficiency.

Figure 3:
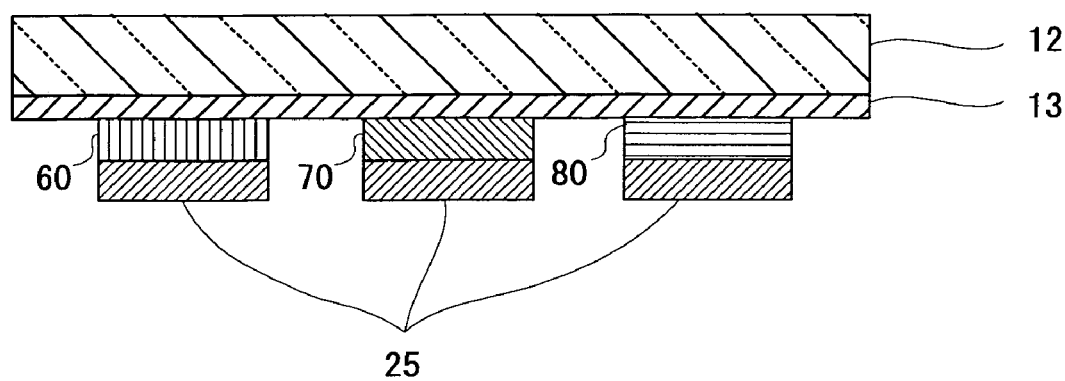
FIG. 3 is a schematic view showing an exemplary configuration of an organic EL display comprising a color conversion layer.
Figure 4:
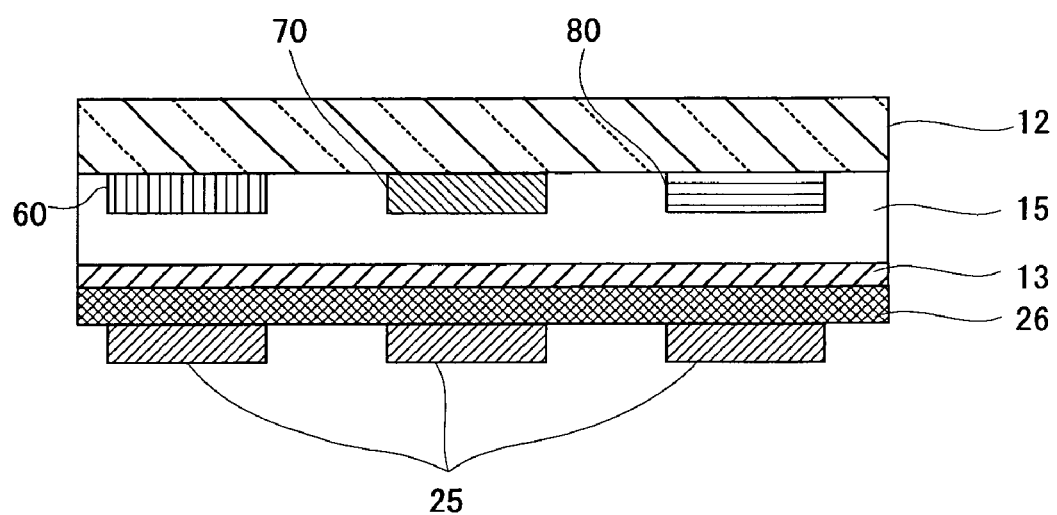
FIG. 4 is a schematic view showing an exemplary configuration of an organic EL display comprising a color conversion layer.

FIG. 3 is a view that illustrates an exemplary configuration of an organic EL display according to three-color light emitting method, and FIG. 4 is a view that illustrates an exemplary configuration of an organic EL display according to white color method. The reference numbers in FIGS. 3 and 4 mean the same reference numbers as in FIG. 2.

When a full color type organic EL display according to the three-color light emitting method is produced by using, for example, the organic EL element of the invention as the element for emitting red light (the organic EL element of the invention may be used as the element for emitting light of other colors, and all colors of light may be emitted by using the organic EL elements of the invention), an organic EL element for emitting green light and organic EL element for emitting blue light are further required.

The organic EL element for emitting blue light is not particularly limited and may be properly selected from those known in the art. Suitable examples thereof include such an organic EL element that has a layer configuration of ITO (positive electrode)/the above-mentioned NPD/Al—Li (negative electrode); and the like.

The organic EL element for emitting green light is not particularly limited and may be properly selected from those known in the art. Suitable examples thereof include such an organic EL element that has a layer configuration of ITO (positive electrode)/NPD aforesaid/Alq aforesaid/Al—Li (negative electrode), and the like.

The configuration of the organic EL display is not particularly limited, may be properly selected depending on the application and may be, for example, a passive-matrix panel or an active-matrix panel as illustrated in "Nikkei Electronics, No. 765, Mar. 13, 2000, pages 55 to 62.".

Figure 5:
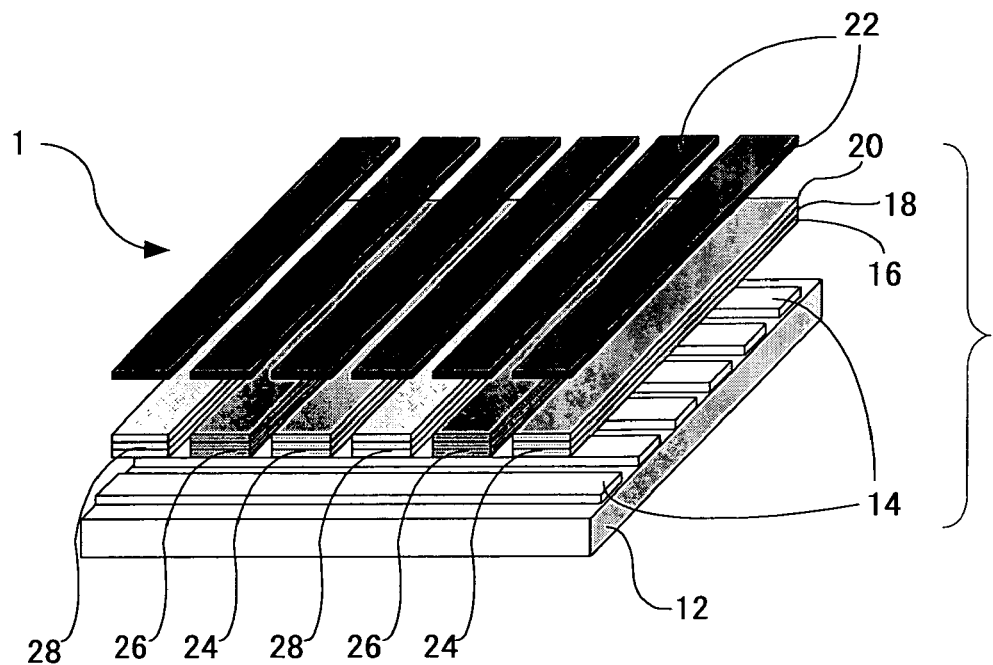
FIG. 5 is a schematic view showing an exemplary configuration of an organic EL display of passive-matrix type or passive-matrix panel.

The passive-matrix panel comprises, for example, glass substrate 12, band-like positive electrodes 14 of e.g. ITO electrodes, organic thin layer 24 for emitting red light, organic thin layer 26 for emitting blue light, organic thin layer 28 for emitting green light, and negative electrodes 22 as shown in FIG. 5. The positive electrodes 14 are arranged in parallel with each other on the glass substrate 12. The organic thin layer 24 for emitting red light, the organic thin layer 26 for emitting blue light, and the organic thin layer 28 for emitting green light are arranged in parallel with one another in turn on the positive electrodes 14 in a direction substantially -perpendicular to the positive electrodes 14. The negative electrodes 22 are arranged on the organic thin layer 24 for emitting red light, the organic thin layer 26 for emitting blue light, and the organic thin layer 28 for emitting green light and have the same shape with these thin layers.

Figure 6:
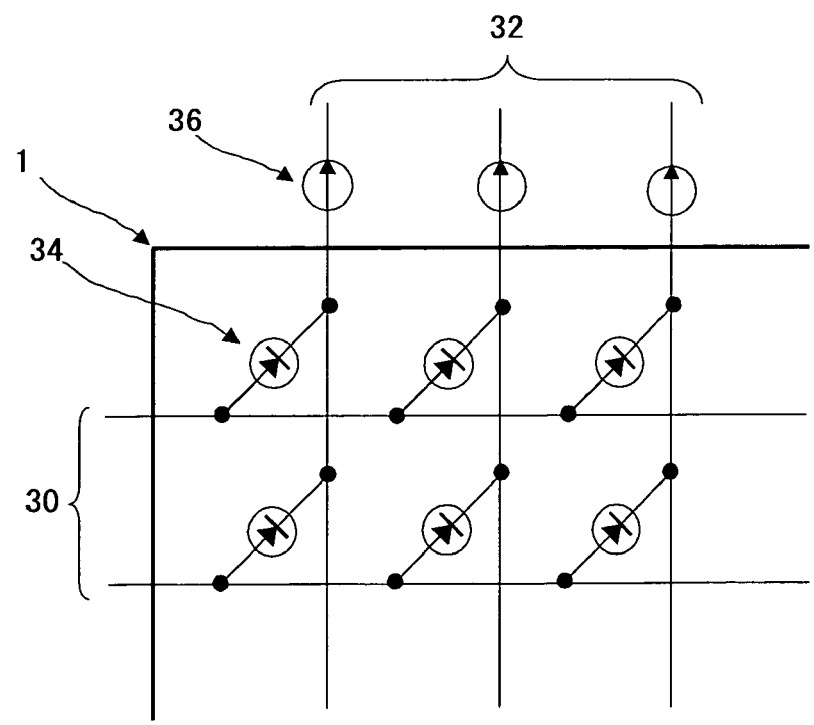
FIG. 6 is a schematic view showing a circuit of an organic EL display of passive-matrix type or passive-matrix panel shown in FIG. 5.

In the passive-matrix panel, for example as shown in FIG. 6, positive electrode lines 30 each having plural positive electrodes 14 intersect negative electrode lines 32 each having plural negative electrodes 22 in a substantially perpendicular direction to form a circuit. The organic thin layers 24, 26, and 28 for emitting, red, blue, and green lights, respectively, are arranged at intersections and serve as pixels. Plural organic EL elements 34 are arranged corresponding to the respective pixels. Upon application of a current by constant-current power supply 36 on one of the positive electrodes 14 in the positive electrode lines 30 and one of the negative electrodes 22 in the negative electrode lines 32 in the passive-matrix panel, the current is applied on an organic EL thin layer at the intersection between the lines to allow the organic EL thin layer at the position to emit light. By controlling light emission of each pixel independently, full-color images can be easily produced.

Figure 7:
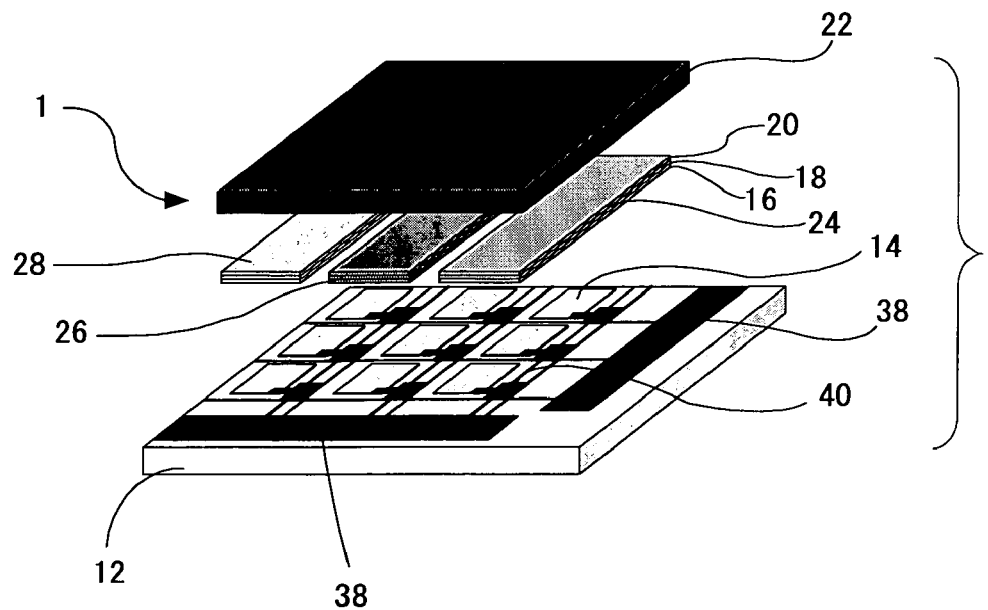
FIG. 7 is a schematic view showing an exemplary configuration of an organic EL display of active-matrix type or active-matrix panel.

With reference to FIG. 7, the active-matrix panel comprises, for example, glass substrate 12, scanning lines, data lines and current supply lines, TFT circuits 40, and positive electrodes 14. The scanning lines, data lines, and current supply lines are arranged on glass substrate 12 as grids in a rectangular arrangement. The TFT circuits 40 are connected typically to the scanning lines constituting the grids and are arranged in each grid. The positive electrodes 14 may be, for example, ITO electrodes, are capable of being driven by the TFT circuits 40 and are arranged in each grid. Organic thin layer 24 for emitting red light, organic thin layer 26 for emitting blue light, and organic thin layer 28 for emitting green red light each has a narrow shape and is arranged in parallel with each other in turn on the positive electrodes 14. Negative electrode 22 is arranged so as to cover these layers. The organic thin layer 24 for emitting red light, the organic thin layer 26 for emitting blue light, and the organic thin layer 28 for emitting green light each comprises hole-injecting layer 16 (not shown), hole-transporting layer 17, light-emitting layer 18, and electron-transporting layer 20.

Figure 8:
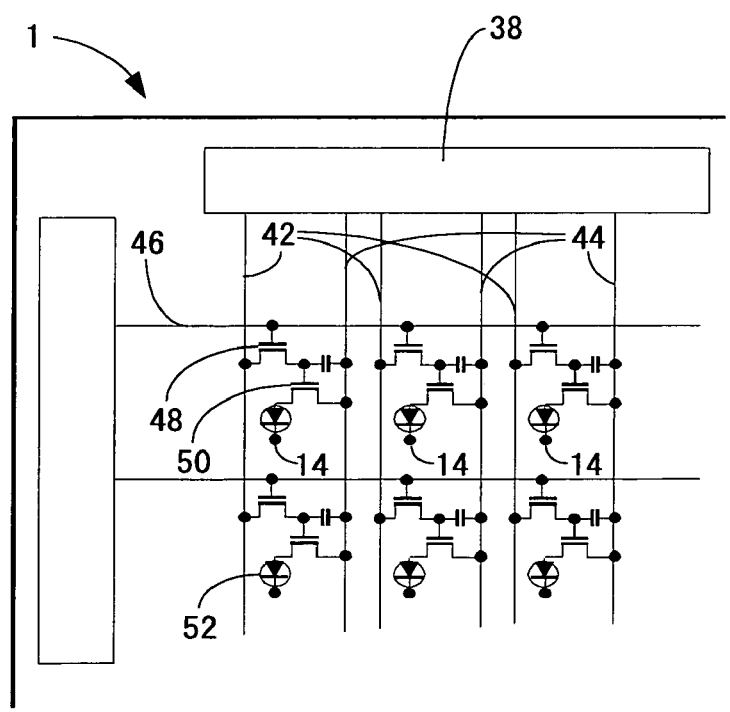
FIG. 8 is a schematic view showing a circuit of an organic EL display of active-matrix type or active-matrix panel shown in FIG. 7.

In the active-matrix panel, for example as shown in FIG. 8, scanning lines 46 intersect with data lines 42 and current-supply lines 44 in a perpendicular direction to form grids in a rectangular arrangement. The scanning lines 46 are arranged in parallel with one another. The data lines 42 and current-supply lines 44 are arranged in parallel with one another. Switching TFT 48 and drive TFT 50 are arranged in each grid to form a circuit. The switching TFT 48 and the drive TFT 50 in each grid can be independently derived by the application of a current by drive circuit 38. In each grid, the organic thin film elements 24, 26 and 28 for emitting blue, green, and red lights, respectively serve as pixels. Upon application of a current from the drive circuit 38 to one of the scanning lines 46 arranged in a lateral direction and to the current-supply lines 44 arranged in a vertical direction, switching TFT 48 positioned at the intersection operates to drive the drive TFT 50 to allow organic EL element 52 at the position to emit light. By controlling light emission of each pixel independently, a full-color image can be easily produced.

The invention will be illustrated with reference to several examples below, which are not intended to limit the scope of the invention.

SYNTHETIC EXAMPLE 1

Synthesis of Pt(isophthalidine-di(n-butylamine))chloride

Isophthalidine-di(n-butylamine)(the tridentate ligand) was synthesized as follows. Specifically, 2 equivalents of n-butylamine (146 mg; 2 mmol) were added to isophthalaldehyde (134 mg; 1 mmol) which was dissolved in absolute ethanol, and the mixture was refluxed for 3 hours. The obtained reaction liquid was cooled and concentrated. Then, the precipitated solid was separated by filtration and was recrystallized using methanol thereby to obtain 200 mg of isophthalidine-di(n-butylamine) of interest.

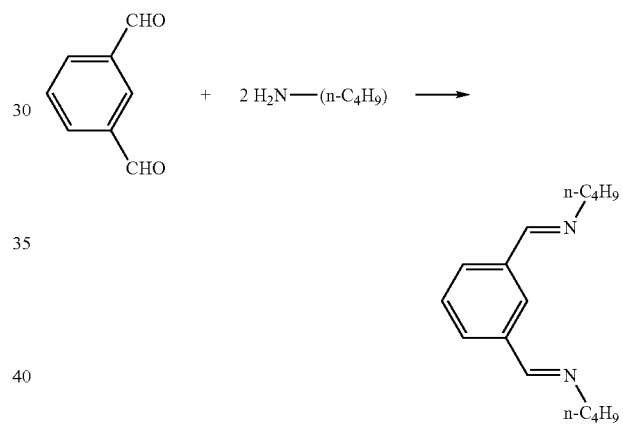

Pt(isophthalidine-di(n-butylamine))chloride was synthesized as follows. Specifically, the obtained isophthalidine-di(n-butylamine) (24 mg; 0.1 mmol) was dissolved in a deaerated solution of acetic acid (10 ml), then 1 equivalent of $K_2PtCl_4$ (42 mg; 0.1 mmol) was added to this, and the mixture was refluxed for 3 days at 120° C. The mixture was cooled and filtered. The solid was washed well with methanol, water and diethyl ether, and was vacuum dried. The obtained raw powder was recrystallized using dichloromethane to obtain 25 mg of Pt(isophthalidine-di(n-butylamine))chloride (Compound 1) of interest.

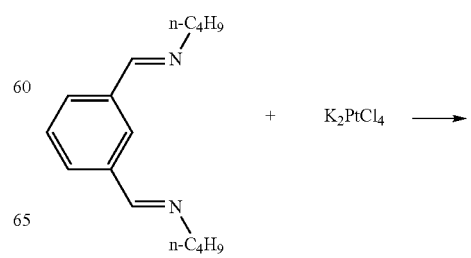

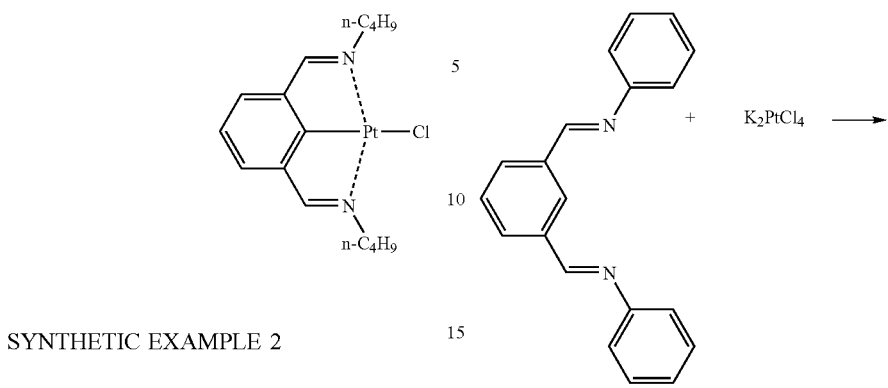

SYNTHETIC EXAMPLE 2

Synthesis of Pt(isophthalidine-dianiline)chloride

Isophthalidine-dianiline (the tridentate ligand) was synthesized as follows. Specifically, 2 equivalents of aniline (186 mg; 2 mmol) were added to isophthalaldehyde (134 mg; 1 mmol) which was dissolved in methanol, and the mixture was stirred for 3 hours. The obtained reaction liquid was concentrated. Then, the precipitated solid was separated by filtration and was recrystallized using methanol thereby to obtain 220 mg of isophthalidine-dianiline of interest.

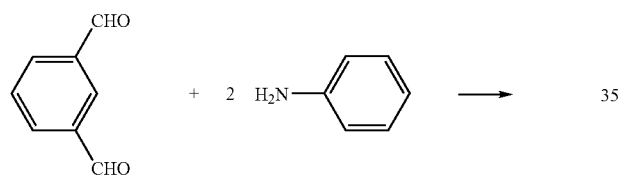

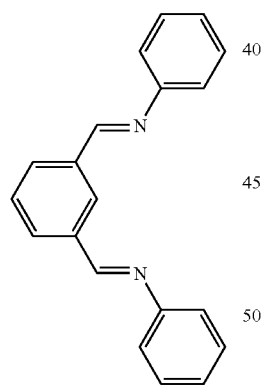

Pt(isophthalidine-dianiline)chloride was synthesized as follows. Specifically, the obtained isophthalidine-dianiline (28 mg; 0.1 mmol) was dissolved in a deaerated solution of acetic acid (10 ml), then 1 equivalent of $K_2PtCl_4$ (42 mg; 0.1 mmol) was added to this, and the mixture was refluxed for 3 days at 120° C. The mixture was cooled and filtered. The solid was washed well with methanol, water and diethyl ether, and was vacuum dried. The obtained raw powder was recrystallized using dichloromethane to obtain 30 mg of Pt(isophthalidine-dianiline)chloride (Compound 2) of interest.

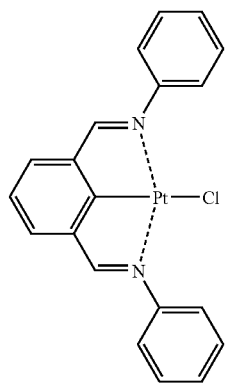

SYNTHETIC EXAMPLE 3

Synthesis of Pt(isophthalidine-di(p-anisole))chloride

Pt(isophthalidine-di(p-anisole))chloride (Compound3) expressed by the following structural formula (51) was obtained in the same way as in Synthetic Example 2, except that, in Synthetic Example 2, p-anisole was used instead of aniline.

structural formula (51)

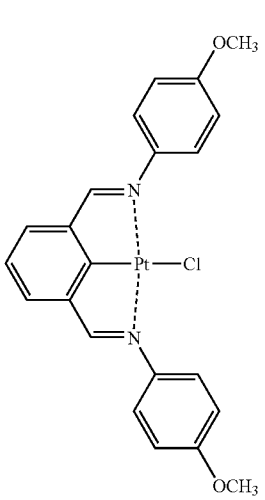

SYNTHETIC EXAMPLE 4

Synthesis of Pt(isophthalidine-dianiline) phenoxide

Pt(isophthalidine-dianiline)chloride (51 mg; 0.1 mmol), which was obtained by the synthetic method of Synthetic Example 2, was added to acetone and stirred. Into this, 1.2 equivalent of sodium phenoxide trihydrate (20 mg; 0.12 mmol), which was dissolved in methanol, was allowed to drip slowly, and stirred for 10 minutes at room temperature. When adding a few drops of pure water, the reaction proceeded, and solid began to precipitate. Therefore, the mixture was stirred for three hours while heating. The mixture was cooled and filtered. The solid was washed well with pure water, methanol, and diethyl ether in order, and was vacuum dried to obtain 40 mg of Pt(isophthalidine-dianiline)phenoxide (Compound 4) of interest.

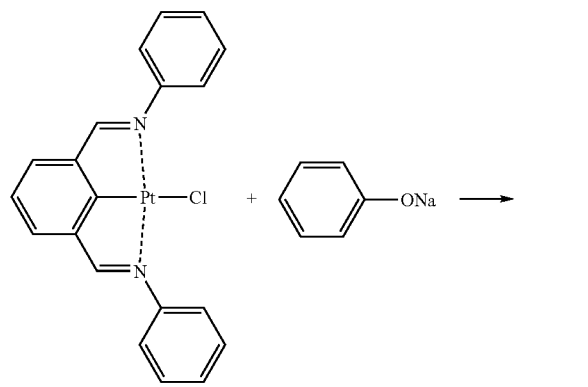

SYNTHETIC EXAMPLE 5

Synthesis of Pt(isophthalidine-dianiline)(1,2,4-triazolate)

The Pt(isophthalidine-dianiline)chloride (51 mg; 0.1 mmol), obtained by the synthetic method of Synthetic Example 2, was added to acetone and stirred. To this, 1.2 equivalent of sodium salt of 1,2,4-triazole (11 mg; 0.12 mmol), which was dissolved in methanol, was allowed to drip slowly, and stirred for 10 minutes at room temperature. When adding a few drops of pure water, the reaction proceeded, and solid began to precipitate. Therefore, the mixture was stirred for three hours while heating. The mixture was cooled and filtered. The solid was washed well with pure water, methanol, and diethyl ether in order, and was vacuum dried to obtain 35 mg of Pt(-isophthalidine-dianiline)(1,2,4-triazolate) (Compound 5) of interest.

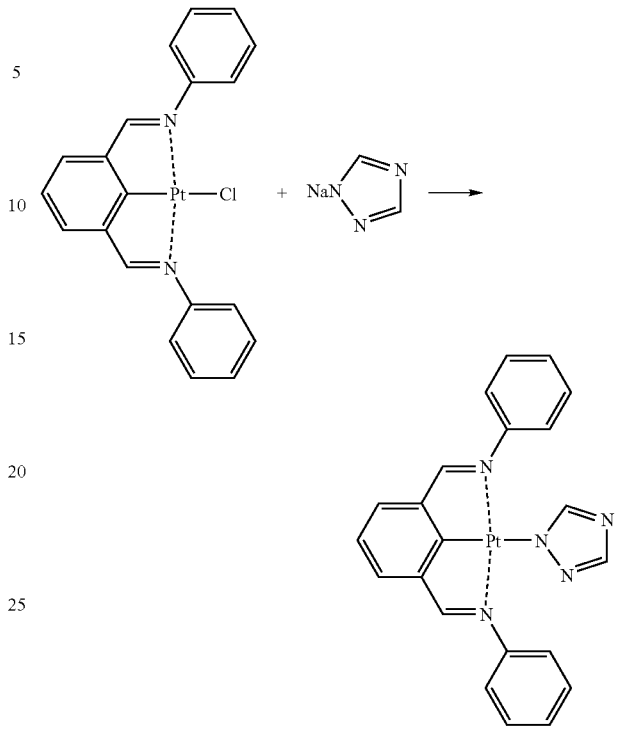

SYNTHETIC EXAMPLE 6

Synthesis of Pt(isophthalidine-dianiline)(2-mercaptobenzothiazolate)

The Pt(isophthalidine-dianiline)chloride (51 mg; 0.1 mmol), obtained by the synthetic method of Synthetic Example 2, was added to acetone and stirred. To this, 1.2 equivalent of 2-mercaptobenzothiazole (20 mg; 0.12 mmol), which was dissolved in methanol, was allowed to drip slowly. Further, 10 equivalent of sodium hydroxide powder (40 mg; 1 mmol) was added and the mixture was refluxed for 5 hours. When the mixture was cooled and a large amount of pure water was added thereto, a solid precipitated. Further, the mixture was stirred for two hours at room temperature. The precipitated solid was filtered, and the solid obtained after filtration was washed well with pure water, methanol, and diethyl ether in order, and was vacuum dried to obtain 35 mg of Pt(isophthalidine-dianiline)(2-mercaptobenzothiazolate) (Compound 6) of interest.

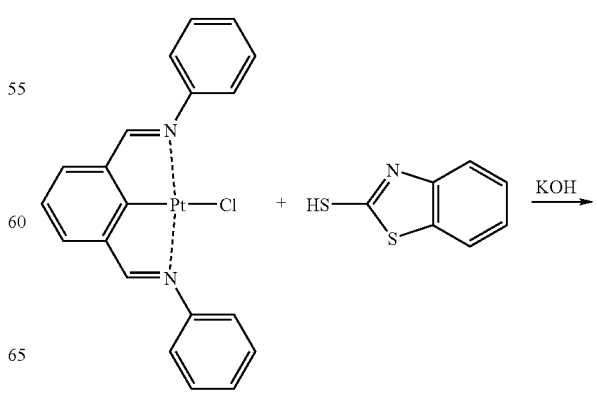

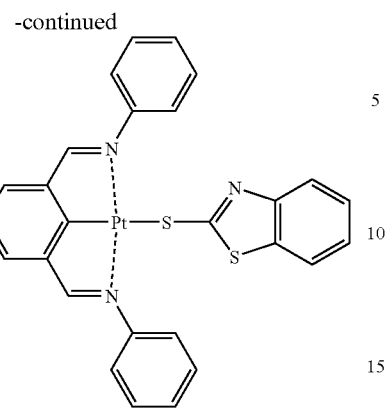

SYNTHETIC EXAMPLE 7

Synthesis of Pt(isophthalidine-dianiline)(phenylacetylide)

The Pt(isophthalidine-dianiline)chloride (51 mg; 0.1 mmol), obtained by the synthetic method of Synthetic Example 2, and 3 equivalent of phenylacetylene (31 mg; 0.3 mmol) were mixed with dichloromethane, and to this, 100 equivalent of triethylamine (1010 mg; 10 mmol) and 5% by mass equivalent of CuI were added and stirred under nitrogen gas stream at room temperature for 24 hours. Dichloromethane was distilled away from the obtained reaction liquid and the remaining oily substance was purified using a flash chromatography (alumina column, eluate: dichloromethane) to obtain 30 mg of Pt(isophthalidine-dianiline)(phenylacetylide) (Compound 7) of interest.

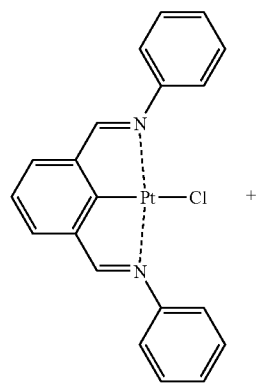 +

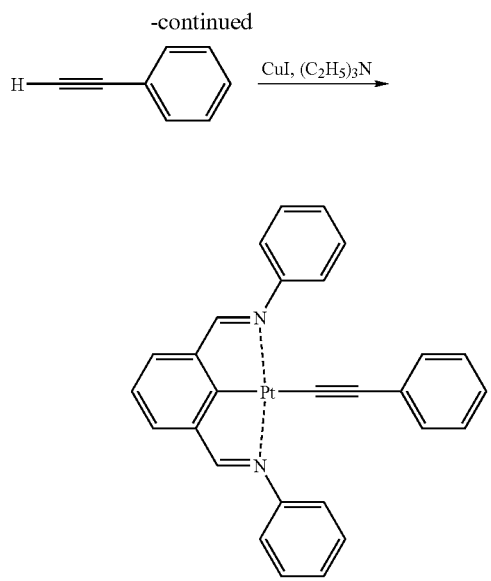

SYNTHETIC EXAMPLE 8 TO 14

Compounds 8 to 14 were synthesized via the following reactions 1 and 2 in the same way as in Synthetic Example 2 except that, in Synthetic Example 2, raw material was replaced with the raw material having Ar and R shown in the following Tables 1 and 2.

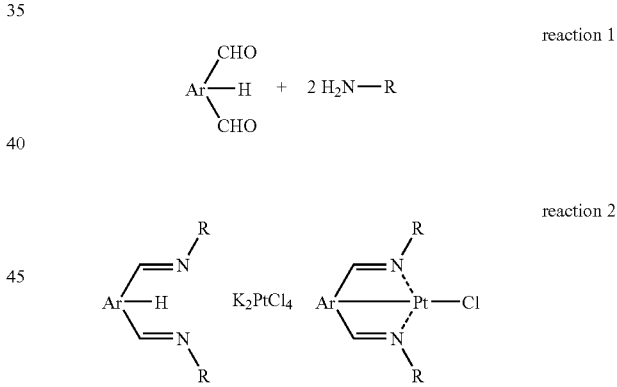

TABLE 1

| R | Ar | | | | |
|---|---|---|---|---|---|
| | Compound 2 | Compound 8 | Compound 9 | Compound 10 | Compound 11 |

TABLE 2

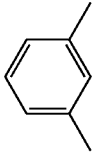

| Ar | Compound 2 | Compound 12 | Compound 13 | Compound 14 |

COMPARATIVE SYNTHETIC EXAMPLE 1

Synthesis of Pt(3,5-di(2-pyridyl)toluene)(phenoxide)(Hereinafter, Described as "Pt(dpt)(oph)")

A tridentate ligand, 3,5-di(2-pyridyl)toluene was synthesized as follows. Specifically, 3,5-dibromotoluene (6.9 g; 20 mmol), 2-tri-n-butylstannylpyridine (26.9 g; 73 mmol), bis(triphenylphosphine)palladium dichloride (1.55 g; 2.2 mmol), and lithium chloride (11.7 g; 276 mmol) were added to 130 ml of toluene and the mixture was refluxed for 2 days. After cooling, 50 ml of saturated potassium fluoride solution was added. The precipitated solid was separated by filtration, washed with a small amount of cooled toluene (20 ml×3), and vacuum dried. The obtained solid was placed to a mixed solution of dichloromethane and NaHCO$_3$, and washed well. The organic layer was separated, was dried over MgSO$_4$ powder, and then the solvent was removed by evaporation. Next, the solid was recrystallized from dichloromethane to obtain 2.2 g of grey solid of 3,5-di(2-pyridyl)toluene of interest.

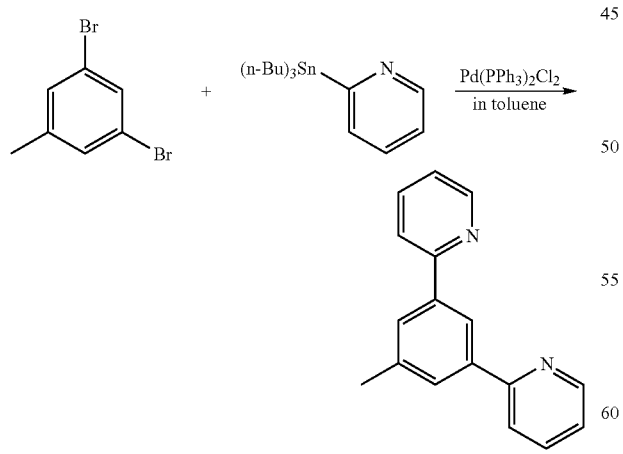

Next, Pt(3,5-di(2-pyridyl)toluene)chloride was synthesized as follows. Specifically, the obtained 3,5-di(2-pyridyl)toluene (300 mg; 1.2 mmol) and K$_2$PtCl$_4$ (550 mg; 1.3 mmol) were placed in a deaerated solution of acetic acid (30 ml), and the mixture was refluxed for 2 days at 130° C. When cooled, a light yellow crystal precipitated. The yellow crystal was filtered, was washed well with methanol, water and diethyl ether, and was vacuum dried. The obtained raw powder was recrystallized using dichloromethane to obtain 436 mg of yellow powder of Pt(3,5-di(2-pyridyl)toluene)chloride of interest.

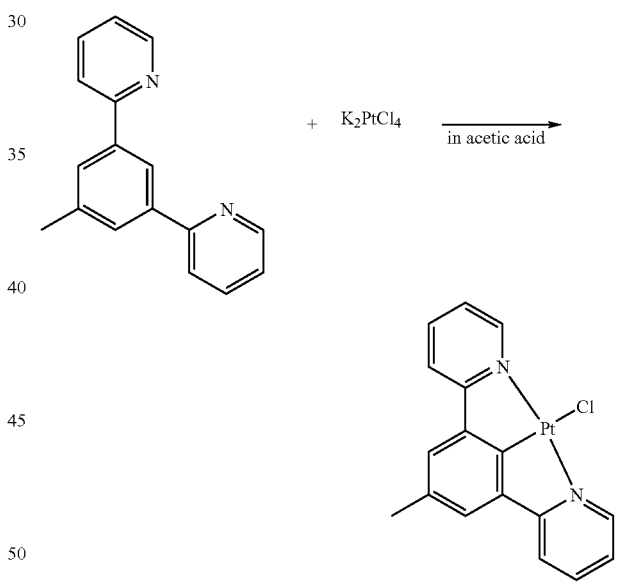

Pt(dpt)(oph) was synthesized as follows. Specifically, 100 mg of the obtained Pt(3,5-di(2-pyridyl)toluene)chloride (0.21 mmol) was added to 30 ml of acetone and stirred. Into this, 53 mg of sodium phenoxide trihydrate (0.32 mmol), which was dissolved in 20 ml of methanol, was allowed to drip slowly, and stirred for 10 minutes at room temperature. When a few drops of water were added, the reaction proceeded, a light yellow solid began to precipitate, and the mixture was stirred for 3 hours while heating. After cooling, the precipitated light yellow solid was filtered, was washed well with pure water, methanol, and diethyl ether in order, and was vacuum dried to obtain a light yellow solid of Pt(dpt)(oph) (Comparative Compound 1) of interest.

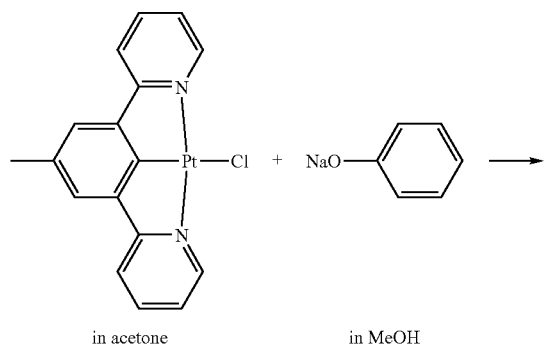

in acetone         in MeOH

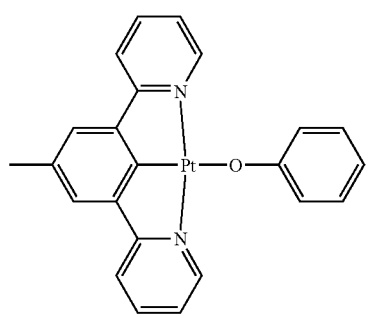

COMPARATIVE SYNTHETIC EXAMPLE 2

Synthesis of Pt(3,5-di(2-pyridyl)toluene)(1,2,4-triazolate) (Hereinafter, Described as "Pt(dpt)(taz)")

100 mg of Pt(3,5-di(2-pyridyl)toluene)chloride (0.21 mmol) was added to 30 ml of acetone and stirred. Into this, 29 mg of sodium salt of 1,2,4-triazole (0.32 mmol), which was dissolved in 20 ml of methanol, was allowed to drip slowly, and stirred for 10 minutes at room temperature. When a few drops of water were added, the reaction proceeded, a yellow solid began to precipitate, and the mixture was stirred for 3 hours while heating. After cooling, the precipitated yellow solid was filtered, was washed well with pure water, methanol, and diethyl ether in order, and was vacuum dried to obtain a yellow solid of Pt(dpt)(taz) (Comparative Compound 2) of interest.

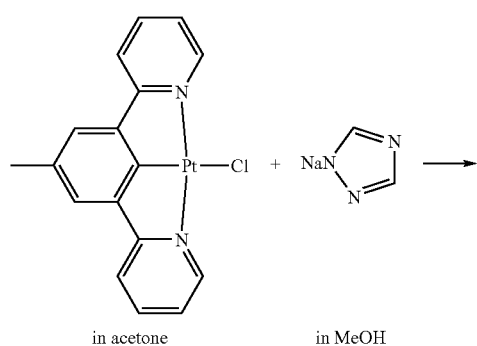

in acetone         in MeOH

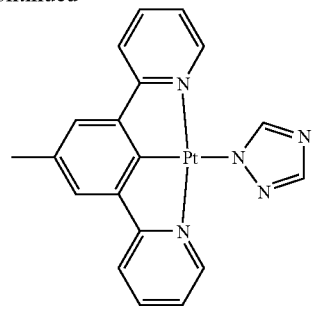

COMPARATIVE SYNTHETIC EXAMPLE 3

Synthesis of Pt(3,5-di(2-pyridyl)toluene)(2-benzothiazoloxalate) (Hereinafter, Described as "Pt(dpt)(obtz)"

100 mg of Pt(3,5-di(2-pyridyl)toluene)chloride (0.21 mmol) and 47.6 mg of 2-hydroxybenzothiazole (0.32 mmol) were added to 30 ml of dimethylsulfoxide (DMSO) and stirred. To this mixture, 200 mg of KOH powder (3.5 mmol) was added and stirred for 10 minutes at room temperature. When a few drops of pure water were added, the reaction proceeded, a yellow solid began to precipitate, and the mixture was stirred for 3 hours while heating. After cooling, the precipitated yellow solid was filtered, was washed well with pure water, methanol, and diethyl ether in order, and was vacuum dried to obtain a, yellow solid of Pt(dpt)(obtz) (Comparative Compound 3) of interest.

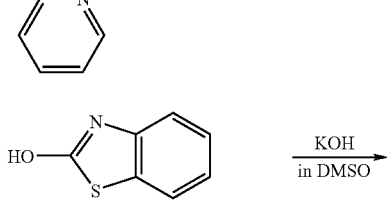

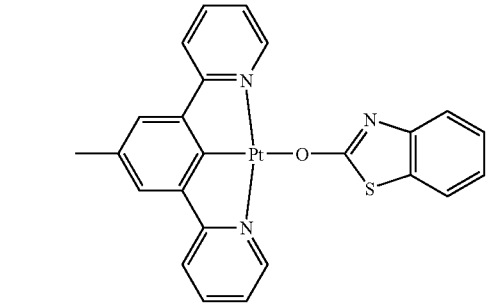

COMPARATIVE SYNTHETIC EXAMPLE 4

Synthesis of Pt(1,3-di(2-pyridyl)benzene)(phenoxide) (Hereinafter, Described as "Pt(dpb)(oph)")

A yellow solid of Pt(dpb)(oph) (Comparative Compound 4) was obtained in the same way as in Comparative Synthetic Example 1, except that, in Comparative Synthetic Example 1, Pt(3,5-di(2-pyridyl)toluene)chloride was changed to Pt(1,3-di(2-pyridyl)benzene)chloride.

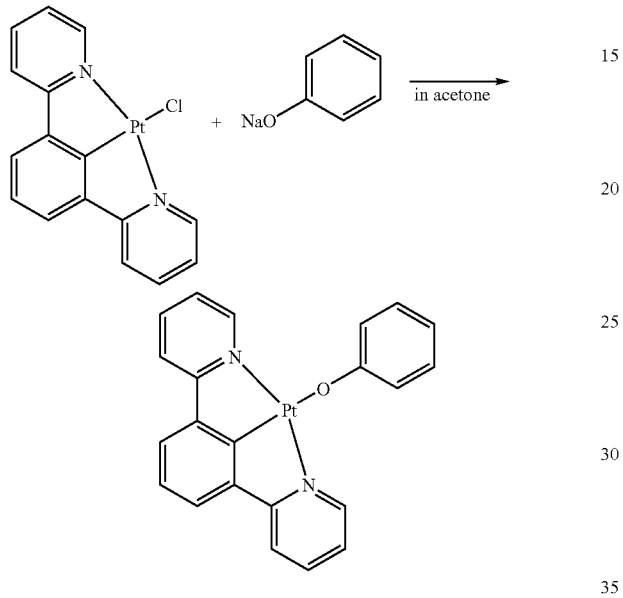

COMPARATIVE SYNTHETIC EXAMPLE 5

Synthesis of Pt(3,5-di(1-isoquinolyl)toluene)(phenoxide) (Hereinafter, Described as "Pt(diqt)(oph)")

An orange solid of Pt(diqt)(oph) (Comparative Compound 5) was obtained in the same way as in Comparative Synthetic Example 1, except that, in Comparative Synthetic Example 1, 2-tri-n-butylstannylpyridine was changed to 2-tri-n-butylstannylisoquinoline to synthesize 3,5-di(1-isoquinolyl)toluene as a tridentate ligand, then Pt(3,5-di(1-isoquinolyl)toluene)chloride was synthesized using the 3,5-di(1-isoquinolyl)toluene and the obtained Pt(3,5-di(1-isoquinolyl)toluene)chloride was used.

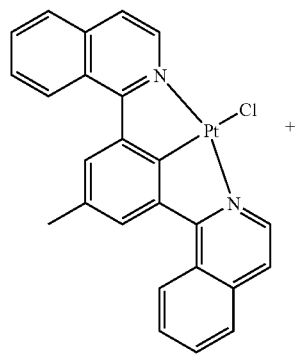

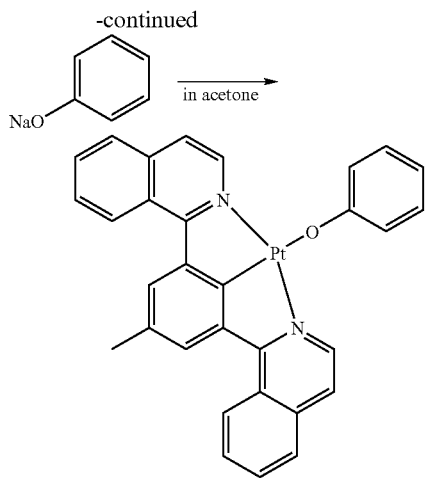

COMPARATIVE SYNTHETIC EXAMPLE 6

Synthesis of Pt(3,5-di(2-pyridyl)pyridine)(phenoxide) (Hereinafter, Described as "Pt(dppr)(oph)")

A yellow solid of Pt(dppr)(oph) (Comparative Compound 6) was obtained in the same way as in Comparative Synthetic Example 1, except that, in Comparative Synthetic Example 1, 3,5-dibromotoluene was changed to 3,5-dibromopyridine to synthesize 3,5-di(2-pyridyl)pyridine as a tridentate ligand, then Pt(3,5-di(2-pyridyl)pyridine)chloride was synthesized using the 3,5-di(2-pyridyl)pyridine and the obtained Pt(3,5-di(2-pyridyl)pyridine)chloride was used.

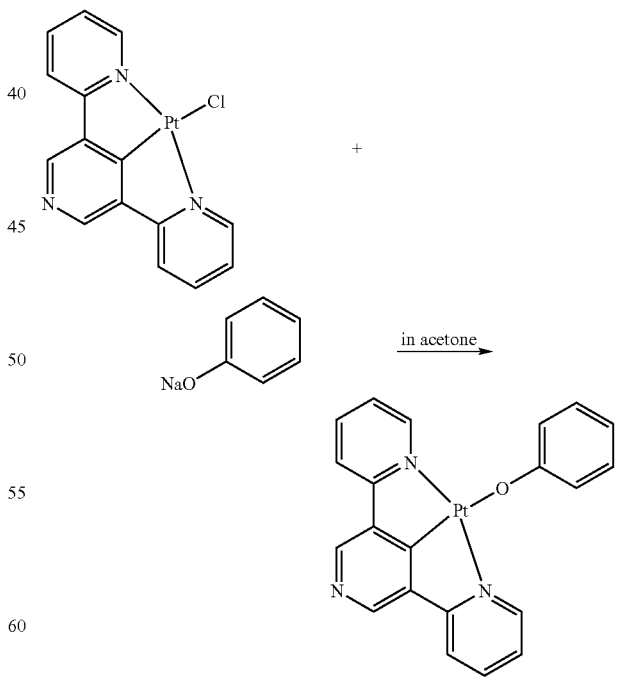

As described above, in Comparative Synthetic Examples 1 to 6, when N^C^N type tridentate ligand is synthesized, organic compounds such as an organotin compound, which is difficult to synthesize and handle, must be used as a raw material. In contrast, the N^C^N type tridentate ligands in Synthetic Examples 1 to 14 can be easily synthesized from a raw material which is stable and easily available.

EXAMPLE 1

A 50 nm thick thin film (luminescent solid) of CBP doped with 2%, based on the ratio of vapor deposition rate, Pt(dPt)(o2Fph), synthesized in Synthetic Example 1, was prepared on a silica glass substrate by co-vapor deposition. The PL (photoluminescence) quantum yield of this thin film (luminescent solid) was determined by the following measurement using as reference a thin film of aluminum quinoline complex (Alq3) of which PL quantum yield is known (PL quantum yield: 22%).

Specifically, the thin film of sample on the transparent substrate was obliquely irradiated with excitation light (365-nm continuous light) from light source. The PL spectrum of the thin film was measured using a spectroradiometer (CS-1000, manufactured by Minolta Co., Ltd.) and PL photon number [P(sample)] was calculated by conversion. Simultaneously with the luminescence measurement, the total intensity of excitation light transmitted through and reflected from the sample [I(sample)] was detected using a photodiode. Subsequently, similar measurement was carried out with respect to the thin film of Alq3 as reference to thereby determine the PL photon number [P(ref.)] and the total intensity of transmitted and reflected excitation light [I(ref)] of reference. Next, the total intensity of transmitted and reflected excitation light of the transparent substrate alone [I(substrate)] was measured. The PL quantum yield of the thin film of the sample can be calculated using the following mathematical formula. The results are shown in Table 3.

$$(PL\ \text{quantum efficiency}) = \frac{P(\text{sample})/[I(\text{substrate}) - I(\text{sample})]}{P(\text{ref.})/[I(\text{substrate}) - I(\text{ref.})]} \times 22\%$$

EXAMPLE 2 TO 14 AND COMPARATIVE EXAMPLES 1 TO 6

The phosphorescent quantum yield of prepared thin film (luminescent solid) was measured in the same way as in Example 1, except that the organometallic complex as a light-emitting material was changed from Compound 1 (Pt(isophthalidine-di(n-butylamine))chloride) to the organometallic complexes described in Table 3 (These were synthesized by the Synthetic Examples mentioned above). The results are shown in Table 3.

TABLE 3

| | Light-emitting Material | Emission Peak (nm) | PL Quantum Yield (%) |
| --- | --- | --- | --- |
| Example 1 | Compound 1 | 507 | 96 |
| Example 2 | Compound 2 | 555 | 85 |
| Example 3 | Compound 3 | 586 | 82 |
| Example 4 | Compound 4 | 601 | 79 |
| Example 5 | Compound 5 | 549 | 92 |
| Example 6 | Compound 6 | 542 | 90 |
| Example 7 | Compound 7 | 549 | 86 |
| Example 8 | Compound 8 | 539 | 78 |
| Example 9 | Compound 9 | 546 | 79 |
| Example 10 | Compound 10 | 605 | 80 |
| Example 11 | Compound 11 | 631 | 70 |
| Example 12 | Compound 12 | 599 | 72 |
| Example 13 | Compound 13 | 532 | 74 |

TABLE 3-continued

| | Light-emitting Material | Emission Peak (nm) | PL Quantum Yield (%) |
| --- | --- | --- | --- |
| Example 14 | Compound 14 | 570 | 73 |
| Comparative Example 1 | Comparative Compound 1 | 523 | 98 |
| Comparative Example 2 | Comparative Compound 2 | 503 | 98 |
| Comparative Example 3 | Comparative Compound 3 | 504 | 94 |
| Comparative Example 4 | Comparative Compound 4 | 511 | 95 |
| Comparative Example 5 | Comparative Compound 5 | 608 | 80 |
| Comparative Example 6 | Comparative Compound 6 | 476 | 85 |

From the results shown in Table 3, it is evident that phosphorescent thin films by the organometallic complex of the invention have a very high phosphorescent quantum yield, which is the same level as that of phosphorescent thin films of Comparative Example.

EXAMPLE 15

Compound 1, (Pt(isophthalidine-di(n-butylamine))chloride), which is the organometallic complex obtained in Synthetic Example 1, was used in a light-emitting layer as a light-emitting material to prepare a multilayered organic EL element. Specifically, a glass substrate with an ITO electrode was washed with water, acetone, and isopropyl alcohol, and a layer of 4,4',4"-tri(2-naphthylphenylamino)triphenylamine (2-TNATA) as a hole-injecting layer of 40 nm thick was formed on the ITO using a vacuum vapor deposition apparatus at a vacuum of $1 \times 10^{-6}$ Torr and at room temperature. Then, a layer of the above-mentioned α-NPD as a hole-transporting layer of 10 nm thick was formed on the hole-injecting layer. A 30 nm thick light-emitting layer of CBP doped with, based on the ratio of vapor deposition rate, 2% by mass of Compound 1, (Pt(isophthalidine-di(n-butylamine))chloride), was formed on the hole-transporting layer. A layer of the above-mentioned BCP as a hole-blocking layer of 20 nm thick was formed on the light-emitting layer. A layer of the Alq as an electron-transporting layer of 20 nm thick was formed on the hole-blocking layer. Further, a layer of LiF was formed to a thickness of 0.5 nm by vapor deposition on the electron-transporting layer, lastly, a layer of aluminum was formed to a thickness of 100 nm by vapor deposition and the element was sealed under the nitrogen atmosphere.

A voltage was applied to the ITO as the positive electrode and the aluminum electrode as the negative electrode in the multilayered organic EL element obtained in this way, and EL properties were measured. Table 4 shows the voltages and current efficiencies at a current density of 5 A/m$^2$.

EXAMPLES 16 TO 28 AND COMPARATIVE EXAMPLES 7 TO 12

Organic EL elements were prepared under the same conditions as Example 15, except that Compound 1 (Pt(isophthalidine-di(n-butylamine))chloride) as a light-emitting material was changed into the organometallic complexes described in Table 4 (those synthesized by the Synthetic Examples mentioned above). A voltage was applied to the ITO as the positive electrode and the aluminum electrode as the negative electrode in these organic EL elements in the same way as in Example 15, and EL properties were measured. Table 4 shows the voltages and current efficiencies at a current density of 5 A/m².

TABLE 4

| | Light-emitting Material | Voltage (V) | Current Efficiency (cd/A) |
|---|---|---|---|
| Example 15 | Compound 1 | 6.3 | 32.3 |
| Example 16 | Compound 2 | 6.2 | 52.5 |
| Example 17 | Compound 3 | 6.4 | 33.6 |
| Example 18 | Compound 4 | 6.4 | 12.4 |
| Example 19 | Compound 5 | 6.3 | 41.5 |
| Example 20 | Compound 6 | 6.4 | 40.9 |
| Example 21 | Compound 7 | 6.3 | 43.5 |
| Example 22 | Compound 8 | 6.4 | 36.5 |
| Example 23 | Compound 9 | 6.3 | 33.2 |
| Example 24 | Compound 10 | 6.5 | 13.1 |
| Example 25 | Compound 11 | 6.5 | 10.3 |
| Example 26 | Compound 12 | 6.3 | 12.1 |
| Example 27 | Compound 13 | 6.4 | 38.3 |
| Example 28 | Compound 14 | 6.4 | 28.1 |
| Comparative Example 7 | Comparative Compound 1 | 6.2 | 59 |
| Comparative Example 8 | Comparative Compound 2 | 6.3 | 55.7 |
| Comparative Example 9 | Comparative Compound 3 | 6.2 | 55.9 |
| Comparative Example 10 | Comparative Compound 4 | 6.3 | 57.3 |
| Comparative Example 11 | Comparative Compound 5 | 5.8 | 13.3 |
| Comparative Example 12 | Comparative Compound 6 | 6.8 | 25.6 |

From the results shown in Table 4, it is evident that organic EL elements of the invention (Examples 15 to 28) exhibit a high EL efficiency, which is the same level as that of organic EL elements of Comparative Examples.

The organometallic complex or luminescent solid of the invention emits light by phosphorescence and can be suitably utilized as a light-emitting material, color conversion material, etc. in organic EL elements, lighting apparatuses, etc.

The organic EL element of the invention uses the organometallic complex, thus may represent excellent luminous efficiency, color conversion efficiency, etc., may be appropriately utilized in a variety of regions such as computers, on-vehicle displays, outdoor displays, household appliances, commercial equipment, household equipment, traffic displays, clock displays, calendar displays, luminescent screens, and audio equipment; in addition, may be preferably utilized for lighting apparatuses and the following organic EL display of the invention.

The organic EL display of the invention uses the organic EL element, thus represents high quality and can be suitably utilized in a variety of regions such as televisions, mobilephones, computers, on-vehicle displays, outdoor displays, household appliances, commercial equipment, household equipment, traffic displays, clock displays, calendar displays, luminescent screens, and audio equipment.

The invention can solve conventional problems and can achieve the above-mentioned objects.

The invention also can provide an organometallic complex and luminescent solid that emit high-intensity light by phosphorescence and that are suitable as a light-emitting material, color conversion material, etc. in organic EL elements, lighting apparatuses, etc.

The invention also can provide an organic EL element which uses the organometallic complex or luminescent solid and may represent excellent luminous efficiency, etc.

The invention also can provide an organic EL display which uses the organic EL element, represents high quality, allows a constant average driving current independently of light-emitting pixels, and has satisfactory color balance without changing the light-emitting area; and which is suitable for, e.g. full-color displays.

What is claimed is:

1. An organometallic complex comprising:
   a metal atom;
   a tridentate ligand
   wherein the tridentate ligand binds to the metal atom tridentately via two nitrogen atoms and a carbon atom, and the carbon atom is located between the two nitrogen atoms, and
   wherein the tridentate ligand has two azomethine bonds (—C=N—), and each nitrogen atom in the azomethine bonds coordinates to the metal atom; and
   further comprising a monodentate ligand which binds to the metal atom monodentately, wherein the monodentate ligand is expressed by the following structural formula (30):

where, in the structural formula (30), R represents an aryl group which may have a substituent group.

2. The organometallic complex according to claim 1, wherein the metal atom is Pt.

3. The organometallic complex according to claim 1, which is electrically neutral.

4. The organometallic complex according to claim 1, which exhibits sublimation property in vacuo.

5. The organometallic complex according to claim 1, which is used in one of an organic EL element and a lighting apparatus.

6. A luminescent solid comprising an organometallic complex, wherein the organometallic complex comprises:
   a metal atom; and
   a tridentate ligand
   wherein the tridentate ligand binds to the metal atom tridentately via two nitrogen atoms and a carbon atom, and the carbon atom is located between the two nitrogen atoms, and
   wherein the tridentate ligand has two azomethine bonds (—C=N—), and each nitrogen atom in the azomethine bonds coordinates to the metal atom.

7. An organic EL element comprising:
   a positive electrode;
   a negative electrode; and
   an organic thin layer between the positive electrode and the negative electrode, wherein the organic thin layer comprises an organometallic complex, wherein the organometallic complex comprises:
   a metal atom; and
   a tridentate ligand
   wherein the tridentate ligand binds to the metal atom tridentately via two nitrogen atoms and a carbon atom, and the carbon atom is located between the two nitrogen atoms, and wherein the tridentate ligand has two azomethine bonds (—C=N—), and each nitrogen atom in the azomethine bonds coordinates to the metal atom.

8. The organic EL element according to claim 7, wherein the organic thin layer comprises a light-emitting layer sandwiched between a hole-transporting layer and an electron-transporting layer, wherein the light-emitting layer comprises the organometallic complex as a light-emitting material.

9. The organic EL element according to claim 8, wherein the light-emitting layer comprises the organometallic complex alone.

10. The organic EL element according to claim 8, wherein the light-emitting layer comprises a carbazole derivative expressed by the following structural formula (64):

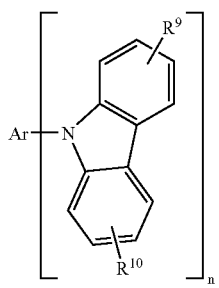

structural formula (64)

where, in the structural formula (64), Ar is a divalent or trivalent group containing an aromatic ring, or a divalent or trivalent group containing a heterocyclic aromatic ring;

$R^9$ and $R^{10}$ represent independently a hydrogen atom, a halogen atom, an alkyl group, an aralkyl group, an alkenyl group, an aryl group, a cyano group, an amino group, an acyl group, an alkoxy carbonyl group, a carboxyl group, an alkoxy group, an alkyl sulfonyl group, a hydroxyl group, an amide group, an aryloxy group, an aromatic hydrocarbon ring or an aromatic heterocyclic group; these may be further substituted by a substituent group; and n represents an integer of 2 or 3.

11. The organic EL element according to claim 8, wherein an electrontransporting material contained in the electron-transporting layer is 2,9-dimethyl-4,7-diphenyl-1,10-phenanthroline (BCP) expressed by the following structural formula (77):

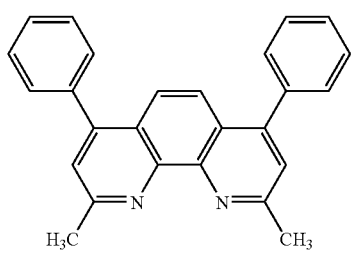

structural formula (77)

12. An organic EL display comprising an organic EL element, wherein the organic EL element comprises:
a positive electrode;
negative electrode; and
an organic thin layer between the positive electrode and the negative electrode, wherein the organic thin layer comprises an organometallic complex, wherein the organometallic complex comprises:
a metal atom; and
a tridentate ligand
wherein the tridentate ligand binds to the metal atom tridentately via two nitrogen atoms and a carbon atom, and the carbon atom is located between the two nitrogen atoms, and
wherein the tridentate ligand has two azomethine bonds (—C=N—), and each nitrogen atom in the azomethine bonds coordinates to the metal atom.

13. The organic EL display according to claim 12, wherein the organic EL display is one of a passive-matrix panel and an active-matrix panel.

* * * * *